US010639194B2

(12) United States Patent
Hunter et al.

(10) Patent No.: US 10,639,194 B2
(45) Date of Patent: *May 5, 2020

(54) HIGH MODULUS POLYMERIC EJECTOR MECHANISM, EJECTOR DEVICE, AND METHODS OF USE

(71) Applicant: Eyenovia, Inc., Tampa, FL (US)

(72) Inventors: Charles Eric Hunter, Boone, NC (US); Louis Thomas Germinario, Kingsport, TN (US); Jonathan Ryan Wilkerson, Raleigh, NC (US); Iyam Lynch, Boone, NC (US); Joshua Richard Brown, Hickory, NC (US)

(73) Assignee: Eyenovia, Inc., New York, NY (US)

( * ) Notice: Subject to any disclaimer, the term of this patent is extended or adjusted under 35 U.S.C. 154(b) by 71 days.

This patent is subject to a terminal disclaimer.

(21) Appl. No.: 15/697,099

(22) Filed: Sep. 6, 2017

(65) Prior Publication Data

US 2018/0116871 A1    May 3, 2018

Related U.S. Application Data

(63) Continuation of application No. 13/712,857, filed on Dec. 12, 2012, now abandoned.
(Continued)

(51) Int. Cl.
*A61M 35/00* (2006.01)
*A61F 9/00* (2006.01)
(Continued)

(52) U.S. Cl.
CPC .......... *A61F 9/0026* (2013.01); *A61F 9/0008* (2013.01); *B05B 17/0646* (2013.01); *B05B 17/0661* (2013.01); *B05B 17/0607* (2013.01)

(58) Field of Classification Search
CPC .. A61F 9/0008; A61F 9/0026; B05B 17/0646; B05B 17/0607; B05B 17/0661
(Continued)

(56) References Cited

U.S. PATENT DOCUMENTS

| 1,482,747 A | 2/1924 | Howe |
| 1,988,637 A | 1/1935 | Tinkham |

(Continued)

FOREIGN PATENT DOCUMENTS

| DE | 19616300 | 10/1997 |
| DE | 199 34 582 | 1/2001 |

(Continued)

OTHER PUBLICATIONS

European Patent Office, International Search Report from PCT/US2012/069296, dated Mar. 20, 2013, 5 pages.
(Continued)

*Primary Examiner* — Andrew J Mensh
(74) *Attorney, Agent, or Firm* — Polsinelli PC

(57) ABSTRACT

An ejector device and method of delivering safe, suitable, and repeatable dosages to a subject for topical, oral, nasal, or pulmonary use is disclosed. The ejector device includes a housing, a reservoir disposed within the housing for receiving a volume of fluid, and an ejector mechanism in fluid communication with the reservoir and configured to eject a stream of droplets, the ejector mechanism comprising an ejector plate coupled to a generator plate and a piezoelectric actuator; the piezoelectric actuator being operable to oscillate the ejector plate, and thereby the generator plate, at a frequency and generate a directed stream of droplets.

12 Claims, 24 Drawing Sheets

Related U.S. Application Data

(60) Provisional application No. 61/591,786, filed on Jan. 27, 2012, provisional application No. 61/569,739, filed on Dec. 12, 2011.

(51) Int. Cl.
*B05B 17/00* (2006.01)
*B05B 17/06* (2006.01)
*B05B 1/08* (2006.01)
*B05B 3/04* (2006.01)
*A61M 11/06* (2006.01)

(58) Field of Classification Search
USPC .............................. 604/295; 239/338, 102.2
See application file for complete search history.

(56) References Cited

U.S. PATENT DOCUMENTS

| | | |
|---|---|---|
| 2,189,643 A | 2/1940 | Ward |
| 2,200,008 A | 5/1940 | Nowak |
| 2,249,608 A | 7/1941 | Greene |
| 2,322,808 A | 6/1943 | Hothersall |
| 2,552,857 A | 5/1951 | Knapp |
| 2,595,317 A | 5/1952 | White |
| 2,987,439 A | 6/1961 | Wittlinger |
| 3,170,462 A | 2/1965 | Hall |
| 3,187,757 A | 6/1965 | Jones et al. |
| 3,237,809 A | 3/1966 | Daragan et al. |
| 3,310,830 A | 3/1967 | Gattone |
| 3,314,426 A | 4/1967 | Caroll |
| 3,439,674 A | 4/1969 | Lelicoff |
| 3,602,399 A | 8/1971 | Litman et al. |
| 3,658,257 A | 4/1972 | Rood |
| 3,709,235 A | 1/1973 | Washburn et al. |
| 3,779,245 A | 12/1973 | Windsor |
| 3,780,950 A | 12/1973 | Brennan |
| 3,795,351 A | 3/1974 | Lehmann |
| 3,812,854 A | 5/1974 | Michaels et al. |
| 3,826,258 A | 7/1974 | Abraham |
| 3,845,764 A | 11/1974 | Windsor |
| 3,892,235 A | 7/1975 | Van Amerongen et al. |
| 3,901,443 A | 8/1975 | Mitsui et al. |
| 3,906,949 A | 9/1975 | Holland |
| 3,913,575 A | 10/1975 | Windsor |
| 3,934,585 A | 1/1976 | Maurice |
| 4,002,168 A | 1/1977 | Petterson |
| 4,012,798 A | 3/1977 | Liautaud |
| 4,052,985 A | 10/1977 | Coleman et al. |
| 4,067,499 A | 1/1978 | Cohen |
| 4,098,431 A | 7/1978 | Palmer et al. |
| D249,709 S | 9/1978 | Trovinger |
| 4,119,096 A | 10/1978 | Drews |
| 4,122,556 A | 10/1978 | Poler |
| 4,131,115 A | 12/1978 | Peng |
| 4,173,226 A | 11/1979 | Shell |
| 4,175,704 A | 11/1979 | Cohen |
| 4,175,706 A | 11/1979 | Gerstmann |
| 4,264,837 A | 4/1981 | Gaboriaud |
| 4,296,071 A | 10/1981 | Weiss et al. |
| 4,319,155 A | 3/1982 | Nakai et al. |
| 4,323,530 A | 4/1982 | Voss et al. |
| 4,338,936 A | 7/1982 | Nelson |
| 4,356,528 A | 10/1982 | Coffee |
| 4,381,533 A | 4/1983 | Coffee |
| 4,388,343 A | 6/1983 | Voss et al. |
| 4,390,542 A | 6/1983 | Schachar |
| 4,398,909 A | 8/1983 | Portnoff |
| 4,465,234 A | 8/1984 | Maehara et al. |
| 4,471,890 A | 9/1984 | Dougherty |
| 4,476,515 A | 10/1984 | Coffee |
| 4,479,609 A | 10/1984 | Maeda et al. |
| 4,493,119 A | 1/1985 | Baumann |
| 4,533,082 A | 8/1985 | Maehara et al. |
| 4,543,096 A | 9/1985 | Keene |
| 4,544,570 A | 10/1985 | Plunkett et al. |
| 4,564,016 A | 1/1986 | Maurice et al. |
| 4,580,721 A | 4/1986 | Coffee et al. |
| 4,605,167 A | 8/1986 | Maehara |
| 4,605,398 A | 8/1986 | Herrick |
| 4,627,845 A | 12/1986 | DeMotte |
| 4,641,384 A | 2/1987 | Landsberger et al. |
| 4,642,581 A | 2/1987 | Erickson |
| 4,658,290 A | 4/1987 | McKenna et al. |
| 4,659,014 A | 4/1987 | Soth et al. |
| 4,679,551 A | 7/1987 | Anthony |
| 4,685,906 A | 8/1987 | Murphy |
| 4,701,167 A | 10/1987 | Chekan |
| 4,702,418 A | 10/1987 | Carter et al. |
| 4,706,848 A | 11/1987 | D'Andrade |
| 4,740,206 A | 4/1988 | Allander |
| 4,742,713 A | 5/1988 | Abe et al. |
| 4,750,650 A | 6/1988 | Ling |
| 4,750,902 A | 6/1988 | Wuchinich et al. |
| 4,758,237 A | 7/1988 | Sacks |
| 4,758,727 A | 7/1988 | Tomei et al. |
| 4,759,755 A | 7/1988 | Hein et al. |
| 4,779,768 A | 10/1988 | St. Amand |
| 4,784,652 A | 11/1988 | Wikström |
| 4,790,479 A | 12/1988 | Matsumoto et al. |
| 4,792,334 A | 12/1988 | Py |
| 4,793,339 A | 12/1988 | Matsumoto et al. |
| 4,796,807 A | 1/1989 | Bendig et al. |
| 4,798,599 A | 1/1989 | Thomas |
| 4,809,914 A | 3/1989 | Goncalves |
| 4,815,661 A | 3/1989 | Anthony |
| 4,826,025 A | 5/1989 | Abiko et al. |
| 4,850,534 A | 7/1989 | Takahashi et al. |
| 4,863,073 A | 9/1989 | Burt et al. |
| 4,863,443 A | 9/1989 | Hornung |
| 4,863,457 A | 9/1989 | Lee |
| 4,871,091 A | 10/1989 | Preziosi |
| 4,877,989 A | 10/1989 | Drews et al. |
| 4,880,146 A | 11/1989 | Hudgins |
| 4,881,283 A | 11/1989 | Liautaud |
| 4,886,189 A | 12/1989 | Vanderjagt |
| 4,896,832 A | 1/1990 | Howlett |
| 4,908,024 A | 3/1990 | Py |
| 4,912,357 A | 3/1990 | Drews et al. |
| 4,917,274 A | 4/1990 | Asa et al. |
| 4,927,062 A | 5/1990 | Walsh |
| 4,927,115 A | 5/1990 | Bahroos et al. |
| 4,946,452 A | 8/1990 | Py |
| 4,952,212 A | 8/1990 | Booth et al. |
| 4,961,885 A | 10/1990 | Avrahami et al. |
| 4,969,869 A | 11/1990 | Burgin et al. |
| 4,981,479 A | 1/1991 | Py |
| 4,996,502 A | 2/1991 | Endo |
| 5,007,905 A | 4/1991 | Bauer |
| 5,019,037 A | 5/1991 | Wang et al. |
| 5,029,579 A | 7/1991 | Trammell |
| 5,030,214 A | 7/1991 | Spector |
| 5,032,111 A | 7/1991 | Morris et al. |
| 5,037,012 A | 8/1991 | Langford |
| 5,040,706 A | 8/1991 | Davis et al. |
| 5,047,009 A | 9/1991 | Morris et al. |
| 5,048,727 A | 9/1991 | Vlasich |
| 5,053,000 A | 10/1991 | Booth et al. |
| 5,054,477 A | 10/1991 | Terada et al. |
| 5,064,420 A | 11/1991 | Clarke et al. |
| 5,066,276 A | 11/1991 | Wang |
| 5,069,204 A | 12/1991 | Smith et al. |
| 5,069,675 A | 12/1991 | Menchel et al. |
| 5,085,651 A | 2/1992 | Py |
| 5,098,375 A | 3/1992 | Baier |
| 5,133,702 A | 7/1992 | Py |
| 5,134,993 A | 8/1992 | van der Linden et al. |
| 5,139,496 A | 8/1992 | Hed |
| 5,145,113 A | 9/1992 | Burwell et al. |
| 5,152,435 A | 10/1992 | Stand et al. |
| 5,152,456 A | 10/1992 | Ross et al. |
| 5,163,929 A | 11/1992 | Py |
| 5,164,740 A | 11/1992 | Ivri |
| 5,170,782 A | 12/1992 | Kocinski |

(56) References Cited

U.S. PATENT DOCUMENTS

| | | |
|---|---|---|
| 5,171,306 A | 12/1992 | Vo |
| 5,178,856 A | 1/1993 | Takahashi et al. |
| 5,193,745 A | 3/1993 | Holm |
| 5,201,726 A | 4/1993 | Kirkham |
| 5,203,506 A | 4/1993 | Gross et al. |
| 5,226,538 A | 7/1993 | Roselle |
| 5,252,318 A | 10/1993 | Joshi et al. |
| 5,259,385 A | 11/1993 | Miller et al. |
| 5,261,601 A | 11/1993 | Ross et al. |
| 5,265,288 A | 11/1993 | Allison |
| 5,267,986 A | 12/1993 | Py |
| 5,276,867 A | 1/1994 | Kenley et al. |
| 5,296,673 A * | 3/1994 | Smith .................. B41M 5/24 219/121.68 |
| 5,299,739 A | 4/1994 | Takahashi et al. |
| 5,316,159 A | 5/1994 | Douglas et al. |
| 5,318,014 A | 6/1994 | Carter |
| 5,320,845 A | 6/1994 | Py |
| 5,354,032 A | 10/1994 | Sims et al. |
| 5,364,405 A | 11/1994 | Zaleski |
| 5,368,582 A | 11/1994 | Bertera |
| 5,401,259 A | 3/1995 | Py |
| 5,405,614 A | 4/1995 | D'Angelo et al. |
| 5,431,663 A | 7/1995 | Carter |
| 5,435,282 A | 7/1995 | Haber et al. |
| 5,435,465 A | 7/1995 | El-Amin |
| 5,462,586 A | 10/1995 | Sugiyama et al. |
| 5,485,828 A | 1/1996 | Hauser |
| 5,496,411 A | 3/1996 | Candy |
| 5,499,751 A | 3/1996 | Meyer |
| D368,774 S | 4/1996 | Py |
| 5,515,841 A | 5/1996 | Robertson et al. |
| 5,518,179 A | 5/1996 | Humberstone et al. |
| 5,529,055 A | 6/1996 | Gueret |
| D374,719 S | 10/1996 | Py |
| 5,564,016 A | 10/1996 | Korenshtein |
| 5,584,823 A | 12/1996 | Valberg |
| 5,586,550 A | 12/1996 | Ivri et al. |
| 5,588,564 A | 12/1996 | Hutson et al. |
| 5,607,410 A | 3/1997 | Branch |
| 5,613,957 A | 3/1997 | Py |
| 5,614,545 A | 3/1997 | Martin et al. |
| 5,630,793 A | 5/1997 | Rowe |
| 5,657,926 A | 8/1997 | Toda |
| 5,665,079 A | 9/1997 | Stahl |
| 5,685,869 A | 11/1997 | Py |
| 5,687,874 A | 11/1997 | Omori et al. |
| 5,707,636 A | 1/1998 | Rodriguez et al. |
| 5,724,021 A | 3/1998 | Perrone |
| 5,730,723 A | 3/1998 | Castellano et al. |
| 5,735,811 A | 4/1998 | Brisken |
| 5,740,947 A | 4/1998 | Flaig et al. |
| 5,746,728 A | 5/1998 | Py |
| 5,758,637 A | 6/1998 | Ivri et al. |
| 5,803,106 A | 9/1998 | Cohen et al. |
| 5,807,357 A | 9/1998 | Kang |
| 5,823,428 A | 10/1998 | Humberstone et al. |
| 5,838,350 A | 11/1998 | Newcombe et al. |
| 5,843,109 A | 12/1998 | Mehta et al. |
| 5,855,322 A | 1/1999 | Py |
| 5,881,956 A | 3/1999 | Cohen et al. |
| 5,893,515 A | 4/1999 | Hahn et al. |
| 5,894,841 A | 4/1999 | Voges |
| 5,938,117 A | 8/1999 | Ivri |
| D413,668 S | 9/1999 | Mannberg et al. |
| 5,957,943 A | 9/1999 | Vaitekunas |
| 5,970,974 A | 10/1999 | Van Der Linden et al. |
| 5,996,903 A | 12/1999 | Asai et al. |
| 5,997,518 A | 12/1999 | Laibovitz et al. |
| 6,008,468 A | 12/1999 | Tanaka et al. |
| 6,011,062 A | 1/2000 | Schneider et al. |
| 6,027,450 A | 2/2000 | Brown |
| 6,039,565 A | 3/2000 | Chou et al. |
| 6,062,212 A | 5/2000 | Davison et al. |
| 6,083,922 A | 7/2000 | Montgomery |
| 6,085,740 A | 7/2000 | Ivri et al. |
| 6,135,427 A | 10/2000 | Tsai |
| 6,152,383 A | 11/2000 | Chen |
| 6,159,188 A | 12/2000 | Laibovitz et al. |
| 6,193,683 B1 | 2/2001 | Ludin et al. |
| 6,203,759 B1 | 3/2001 | Pelc et al. |
| 6,216,966 B1 | 4/2001 | Prendergast et al. |
| 6,221,038 B1 | 4/2001 | Brisken |
| 6,228,046 B1 | 5/2001 | Brisken |
| 6,235,024 B1 | 5/2001 | Tu |
| 6,254,579 B1 | 7/2001 | Cogger et al. |
| 6,254,587 B1 | 7/2001 | Christ et al. |
| 6,263,872 B1 | 7/2001 | Schuster et al. |
| 6,273,342 B1 | 8/2001 | Terada et al. |
| 6,296,626 B1 | 10/2001 | Stein |
| 6,318,361 B1 | 11/2001 | Sosiak |
| 6,336,917 B1 | 1/2002 | Berke |
| 6,341,732 B1 | 1/2002 | Martin et al. |
| 6,357,442 B1 | 3/2002 | Casper et al. |
| 6,357,671 B1 | 3/2002 | Cewers |
| 6,367,685 B1 | 4/2002 | Jiang et al. |
| 6,394,363 B1 | 5/2002 | Arnott et al. |
| 6,398,737 B2 | 6/2002 | Moore et al. |
| 6,398,766 B1 | 6/2002 | Branch |
| 6,422,431 B2 | 7/2002 | Pelc et al. |
| 6,423,040 B1 | 7/2002 | Benktzon et al. |
| 6,425,888 B1 | 7/2002 | Embleton et al. |
| 6,427,682 B1 | 8/2002 | Klimowicz et al. |
| 6,442,423 B1 | 8/2002 | Domb et al. |
| 6,443,146 B1 | 9/2002 | Voges |
| 6,467,476 B1 | 10/2002 | Ivri et al. |
| 6,526,976 B1 | 3/2003 | Baran |
| 6,530,370 B1 | 3/2003 | Heinonen |
| 6,540,153 B1 | 4/2003 | Ivri |
| 6,540,154 B1 | 4/2003 | Ivri et al. |
| 6,543,443 B1 | 4/2003 | Klimowicz et al. |
| 6,546,927 B2 | 4/2003 | Litherland et al. |
| 6,550,472 B2 | 4/2003 | Litherland et al. |
| 6,554,201 B2 | 4/2003 | Klimowicz et al. |
| 6,554,801 B1 | 4/2003 | Steward et al. |
| 6,569,131 B1 | 5/2003 | Michael et al. |
| 6,569,387 B1 | 5/2003 | Furner et al. |
| 6,601,033 B1 | 8/2003 | Melanson et al. |
| 6,601,581 B1 | 8/2003 | Babaev |
| 6,612,302 B1 | 9/2003 | Rand |
| 6,615,824 B2 | 9/2003 | Power |
| 6,619,562 B2 | 9/2003 | Hamaguchi et al. |
| 6,622,720 B2 | 9/2003 | Hadimioglu |
| 6,629,646 B1 | 10/2003 | Ivri |
| 6,640,804 B2 | 11/2003 | Ivri et al. |
| 6,650,935 B1 | 11/2003 | Watmough |
| 6,651,650 B1 | 11/2003 | Yamamoto et al. |
| 6,659,364 B1 | 12/2003 | Humberstone et al. |
| 6,669,961 B2 | 12/2003 | Kim et al. |
| 6,676,034 B2 | 1/2004 | Tanaka et al. |
| 6,679,436 B1 | 1/2004 | Onishi et al. |
| 6,684,681 B1 | 2/2004 | Zombo |
| 6,684,879 B1 | 2/2004 | Coffee et al. |
| 6,719,770 B2 | 4/2004 | Laufer et al. |
| 6,732,944 B2 | 5/2004 | Litherland et al. |
| 6,736,904 B2 | 5/2004 | Poniatowski et al. |
| 6,740,107 B2 | 5/2004 | Loeb et al. |
| 6,748,944 B1 | 6/2004 | Della Vecchia et al. |
| 6,761,286 B2 | 7/2004 | Py et al. |
| 6,789,741 B2 | 9/2004 | Varanasi et al. |
| 6,814,071 B2 | 11/2004 | Klimowicz et al. |
| 6,851,626 B2 | 2/2005 | Patel et al. |
| 6,854,662 B2 | 2/2005 | Chen |
| 6,863,224 B2 | 3/2005 | Terada et al. |
| 6,877,642 B1 | 4/2005 | Maddox et al. |
| 6,885,818 B2 | 4/2005 | Goldstein |
| 6,901,926 B2 | 6/2005 | Yamamoto et al. |
| 6,913,205 B2 | 7/2005 | Cornet et al. |
| 6,921,020 B2 * | 7/2005 | Ivri .................. A61M 11/005 239/102.2 |
| 6,926,208 B2 | 8/2005 | Ivri |
| 6,946,117 B1 | 9/2005 | Schutt et al. |
| 6,964,647 B1 | 11/2005 | Babaev |
| 6,969,165 B2 | 11/2005 | Olsen |

(56) References Cited

U.S. PATENT DOCUMENTS

| | | |
|---|---|---|
| 6,974,450 B2 | 12/2005 | Weber et al. |
| 6,976,279 B1 | 12/2005 | Berke et al. |
| 6,976,969 B2 | 12/2005 | Messerly |
| 6,978,945 B2 | 12/2005 | Wong et al. |
| 7,017,573 B1 | 3/2006 | Rasor et al. |
| 7,032,590 B2 | 4/2006 | Loeffler et al. |
| 7,040,549 B2 | 5/2006 | Ivri et al. |
| 7,066,398 B2 | 6/2006 | Borland et al. |
| 7,081,757 B2 | 7/2006 | Unsworth et al. |
| 7,083,112 B2 | 8/2006 | Ivri |
| 7,104,463 B2 | 9/2006 | Litherland et al. |
| 7,108,197 B2 | 9/2006 | Ivri |
| 7,121,275 B2 | 10/2006 | Noolandi et al. |
| D533,658 S | 12/2006 | Collins, Jr. et al. |
| 7,153,315 B2 | 12/2006 | Miller |
| 7,161,269 B2 | 1/2007 | Kayama et al. |
| 7,168,633 B2 | 1/2007 | Wang et al. |
| D537,160 S | 2/2007 | Lowell |
| 7,174,888 B2 | 2/2007 | Ivri et al. |
| 7,192,129 B2 | 3/2007 | Droege et al. |
| 7,201,732 B2 | 4/2007 | Anderson et al. |
| 7,204,820 B2 | 4/2007 | Akahoshi |
| 7,229,028 B2 | 6/2007 | Chen et al. |
| 7,234,460 B2 | 6/2007 | Greenleaf et al. |
| 7,314,187 B2 | 1/2008 | Hochrainer et al. |
| 7,316,067 B2 | 1/2008 | Blakey |
| 7,331,339 B2 | 2/2008 | Smith et al. |
| 7,357,133 B2 | 4/2008 | Goodchild |
| 7,472,701 B2 | 1/2009 | Pfichner et al. |
| D597,206 S | 7/2009 | Collins, Jr. et al. |
| 7,574,787 B2 | 8/2009 | Xu et al. |
| 7,678,089 B2 | 3/2010 | Py et al. |
| 7,712,466 B2 | 5/2010 | Addington et al. |
| 7,819,115 B2 | 10/2010 | Sexton et al. |
| 7,883,031 B2 | 2/2011 | Collins, Jr. et al. |
| 7,954,486 B2 | 6/2011 | Papania et al. |
| 8,012,136 B2 | 9/2011 | Collins, Jr. et al. |
| 8,485,503 B2 | 7/2013 | Lei |
| 8,545,463 B2 | 10/2013 | Collins, Jr. et al. |
| 2001/0025190 A1 | 9/2001 | Weber et al. |
| 2001/0049608 A1 | 12/2001 | Hochman |
| 2001/0056258 A1 | 12/2001 | Evans |
| 2002/0016576 A1 | 2/2002 | Lee |
| 2002/0039502 A1 | 4/2002 | Matsumoto et al. |
| 2002/0043262 A1 | 4/2002 | Langford et al. |
| 2002/0073989 A1 | 6/2002 | Hadimioglu |
| 2002/0074362 A1 | 6/2002 | Py et al. |
| 2002/0107492 A1 | 8/2002 | Brach et al. |
| 2002/0121285 A1 | 9/2002 | Poniatowski et al. |
| 2002/0124843 A1 | 9/2002 | Skiba et al. |
| 2002/0161344 A1 | 10/2002 | Peclat et al. |
| 2003/0032930 A1 | 2/2003 | Branch |
| 2003/0078551 A1 | 4/2003 | Hochrainer et al. |
| 2003/0114901 A1 | 6/2003 | Loeb et al. |
| 2003/0144594 A1 | 7/2003 | Gellman |
| 2003/0185892 A1 | 10/2003 | Bell et al. |
| 2003/0192532 A1 | 10/2003 | Hopkins |
| 2004/0010239 A1 | 1/2004 | Hochrainer et al. |
| 2004/0039355 A1 | 2/2004 | Gonzalez et al. |
| 2004/0045547 A1 | 3/2004 | Yamamoto et al. |
| 2004/0050953 A1 | 3/2004 | Terada et al. |
| 2004/0082884 A1 | 4/2004 | Pal et al. |
| 2004/0164099 A1 | 8/2004 | Diestelhorst et al. |
| 2004/0176757 A1 | 9/2004 | Sinelnikov et al. |
| 2004/0186384 A1 | 9/2004 | Babaev |
| 2004/0204674 A1 | 10/2004 | Anderson et al. |
| 2004/0215157 A1 | 10/2004 | Peclat et al. |
| 2004/0256487 A1 | 12/2004 | Collins, Jr. et al. |
| 2005/0001981 A1 | 1/2005 | Anderson et al. |
| 2005/0029307 A1 | 2/2005 | Py et al. |
| 2005/0077315 A1 | 4/2005 | Pavlu et al. |
| 2005/0077392 A1 | 4/2005 | Geser et al. |
| 2005/0089545 A1 | 4/2005 | Kuwano et al. |
| 2005/0195598 A1 | 9/2005 | Dancs et al. |
| 2005/0199236 A1 | 9/2005 | Fink et al. |
| 2005/0240162 A1 | 10/2005 | Chen et al. |
| 2005/0244339 A1 | 11/2005 | Jauernig et al. |
| 2005/0261641 A1 | 11/2005 | Warchol et al. |
| 2005/0263608 A1 | 12/2005 | Ivri |
| 2005/0275310 A1 | 12/2005 | Ripoll |
| 2005/0279350 A1 | 12/2005 | Rasor et al. |
| 2006/0024374 A1 | 2/2006 | Gasco et al. |
| 2006/0057216 A1 | 3/2006 | Salamone et al. |
| 2006/0174869 A1 | 8/2006 | Gumaste et al. |
| 2006/0196518 A1 | 9/2006 | Hon |
| 2006/0201501 A1 | 9/2006 | Morrison et al. |
| 2006/0209129 A1 | 9/2006 | Onozawa |
| 2006/0213503 A1 | 9/2006 | Borgschulte et al. |
| 2006/0243820 A1 | 11/2006 | Ng |
| 2006/0258993 A1 | 11/2006 | Hochrainer et al. |
| 2007/0023547 A1 | 2/2007 | Borland et al. |
| 2007/0044792 A1 | 3/2007 | Ivri |
| 2007/0113841 A1 | 5/2007 | Fuchs |
| 2007/0119968 A1 | 5/2007 | Collins, Jr. et al. |
| 2007/0119969 A1 | 5/2007 | Collins, Jr. et al. |
| 2007/0211212 A1 | 9/2007 | Bennwik |
| 2008/0017189 A1 | 1/2008 | Ruckdeschel et al. |
| 2008/0043061 A1* | 2/2008 | Glezer .................. H02K 33/18 347/53 |
| 2008/0097359 A1 | 4/2008 | Hochrainer et al. |
| 2008/0142624 A1 | 6/2008 | Ivri et al. |
| 2008/0164339 A1 | 7/2008 | Duru |
| 2008/0233053 A1 | 9/2008 | Gross et al. |
| 2008/0299049 A1 | 12/2008 | Stangl |
| 2008/0303850 A1 | 12/2008 | Shin et al. |
| 2008/0308096 A1 | 12/2008 | Borgschulte et al. |
| 2009/0025713 A1 | 1/2009 | Keller et al. |
| 2009/0114742 A1 | 5/2009 | Collins, Jr. |
| 2009/0149829 A1 | 6/2009 | Collins, Jr. |
| 2009/0167812 A1 | 7/2009 | Asai et al. |
| 2009/0192443 A1 | 7/2009 | Collins, Jr. et al. |
| 2009/0212133 A1 | 8/2009 | Collins, Jr. |
| 2009/0027818 A1 | 11/2009 | Valpey et al. |
| 2009/0272818 A1* | 11/2009 | Valpey, III .......... B05B 17/0646 239/102.2 |
| 2010/0044460 A1 | 2/2010 | Sauzade |
| 2010/0211408 A1 | 8/2010 | Park et al. |
| 2010/0222752 A1 | 9/2010 | Collins, Jr. |
| 2010/0283601 A1 | 11/2010 | Tai et al. |
| 2011/0233302 A1 | 9/2011 | Chien-hua et al. |
| 2012/0143152 A1 | 6/2012 | Hunter et al. |
| 2013/0172830 A1 | 7/2013 | Hunter et al. |

FOREIGN PATENT DOCUMENTS

| | | |
|---|---|---|
| EP | 0011269 | 5/1980 |
| EP | 0150571 | 8/1985 |
| EP | 0224352 | 6/1987 |
| EP | 0389665 | 10/1990 |
| EP | 0 590 165 | 4/1994 |
| EP | 0 823 246 | 2/1996 |
| EP | 0 933 138 | 8/1999 |
| EP | 1493410 | 1/2005 |
| FR | 1271341 | 7/1961 |
| GB | 558866 | 7/1942 |
| GB | 1569707 | 7/1980 |
| JP | H04-100557 | 4/1992 |
| JP | 10-506028 | 6/1998 |
| JP | 2005-324051 | 11/2005 |
| JP | 2008-168223 | 7/2008 |
| JP | 2009-072313 | 4/2009 |
| TW | I293898 | 7/1994 |
| WO | 85/00761 | 2/1985 |
| WO | 91/12687 | 8/1991 |
| WO | 91/14468 | 10/1991 |
| WO | 94/13305 | 6/1994 |
| WO | 94/23788 | 10/1994 |
| WO | 95/15822 | 6/1995 |
| WO | 96/06581 | 3/1996 |
| WO | 97/05960 | 2/1997 |
| WO | 97/12687 | 4/1997 |
| WO | 98/19383 | 5/1998 |
| WO | 99/17888 | 4/1999 |
| WO | 00/18455 | 4/2000 |

(56) References Cited

FOREIGN PATENT DOCUMENTS

| WO | 00/66277 | 11/2000 |
|---|---|---|
| WO | 01/03645 | 1/2001 |
| WO | 01/58236 | 8/2001 |
| WO | 01/85245 | 11/2001 |
| WO | 02/28545 | 4/2002 |
| WO | 02/055131 | 7/2002 |
| WO | 2002/062488 | 8/2002 |
| WO | 02/072169 | 9/2002 |
| WO | 03/002045 | 1/2003 |
| WO | 03/002265 | 1/2003 |
| WO | 03/026556 | 4/2003 |
| WO | 03/097139 | 11/2003 |
| WO | 2004/028420 | 4/2004 |
| WO | 2004/050065 | 6/2004 |
| WO | 2004/103478 | 12/2004 |
| WO | 2004/105864 | 12/2004 |
| WO | 2006/006963 | 1/2006 |
| WO | 2006/082588 | 8/2006 |
| WO | 2008/015394 | 2/2008 |
| WO | 2009/148345 | 12/2009 |
| WO | 2011/083379 | 7/2011 |
| WO | 2012/009696 | 1/2012 |
| WO | 2012/009702 | 1/2012 |
| WO | 2012/009706 | 1/2012 |

OTHER PUBLICATIONS

European Patent Office, International Search Report from PCT/US2012/069309, dated Mar. 20, 2013, 5 pages.

"Alcon®: Sharing One Vision," 2009 Annual Report, 46 pages (2009).

Conover (Ed.), "View into the Future of Ophthalmology Treatments," Healthcare Observer, 1(8):2-37 (2009).

Dhand, "Nebulizers That Use a Vibrating Mesh or Plate with Multiple Apertures to Generate Aerosol," Respir Care, 47(12):1406-1418 (2002).

Donnelly et al., "Using ultrasonic atomization to produce an aerosol of micron-scale particles," Review of Scientific Instruments, 76:113301-1-113301-10 (2005).

Durnan et al., "Gold-Chlorine and Gold-Bromine Equilibria in Fused Salts," The Journal of Physical Chemistry, 68(4):847-850 (1964).

Galambos et al., "Drop ejection utilizing sideways actuation of a MEMS piston," Sensors and Actuators A, 141:182-191 (2008).

Hinds, Aerosol Technology: Properties, Behavior, and Measurement of Airborne Particles, pp. 42-71, 111-119, & 294-301 (1999).

Instruction Manual for Omron® Model NE-U03V MicroAir® Nebulizer, 20 pages (No date).

International Search Report dated Dec. 12, 2011, in International Application No. PCT/US2011/044291.

International Search Report dated Dec. 13, 2011, in International Application No. PCT/US2011/044286.

Product Description for Xalatan®: latanoprost ophthalmic solution, Pfizer Manufacturing, Belgium, NV, 8 pages (2009).

Quigley, "Improving Eye Drop Treatment for Glaucoma through Better Adherence," Optometry and Vision Science, 85(6):374-375 (2008).

Ranade et al., "Chapter seven: Intranasal and ocular drug delivery," Drug Delivery Systems: Second Edition, CLC Press, 39 pages (2004).

Rosen et al., "Printing High Viscosity Fluids Using Ultrasonic Droplet Generation," The George W. Woodruff School of Mechanical Engineering, Georgia Institute of Technology, pp. 239-253 (2008).

Shidhaye et al., "Novel drug delivery devices," Pharma Times, 38(7):24-27 (2006).

Tamilvanan et al., "The potential of lipid emulsion for ocular delivery of lipophilic drugs," European Journal of Pharmaceutics and Biopharmaceutics, 58:357-368 (2004).

Xia et al., "A potential application of a piezoelectric atomiser for ophthalmic drug delivery," BOB, 4(1):9-17 (2007).

Yee et al., "Trends in Glaucoma Treatment," EyeWorld Educational Symposium, San Francisco, 8 pages(2006).

Yuan et al., "MEMS-based piezoelectric array microjet," Microelectronic Engineering, 66:767-772 (2003).

Santvliet et al., "Determinents of Eye Drop Size," Survey of Ophthamology, Mar.-Apr. 2004, vol. 49, pp. 197-211.

Brown et al., "The Preservation of Ophthalmic Preparations," Journal of the Society of Cosmetic Chemists, 1965, vol. 16, pp. 369-393.

\* cited by examiner

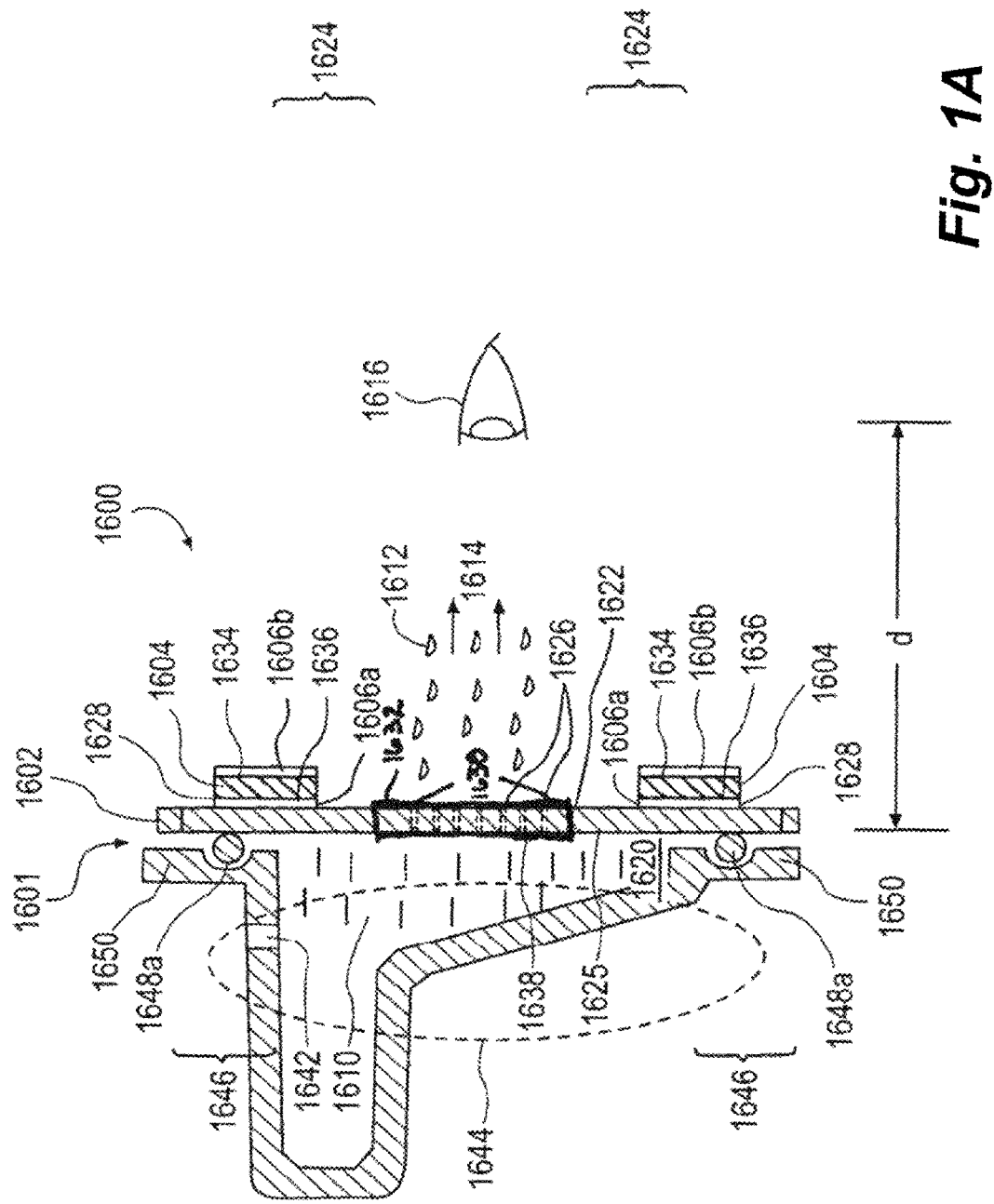

Flute intake diameter

Ejector Face

Capillary length

Reservoir Face

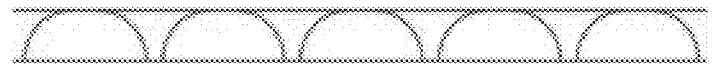
FIG. 14A
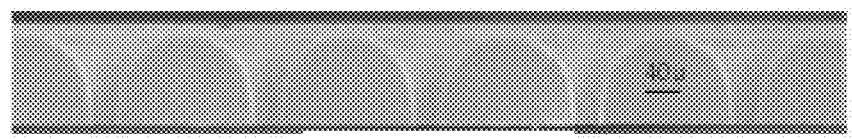
Fig. 14B
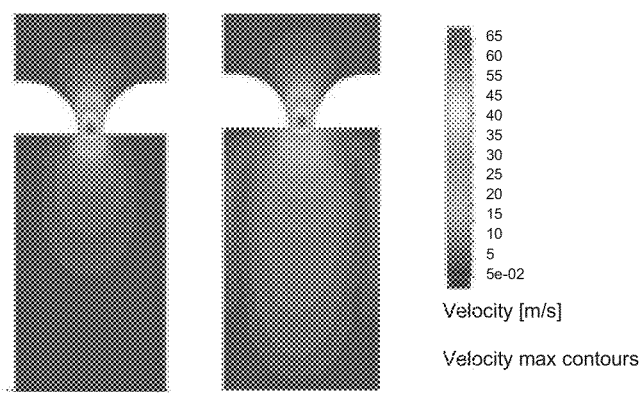
FIG. 15A  FIG. 15B

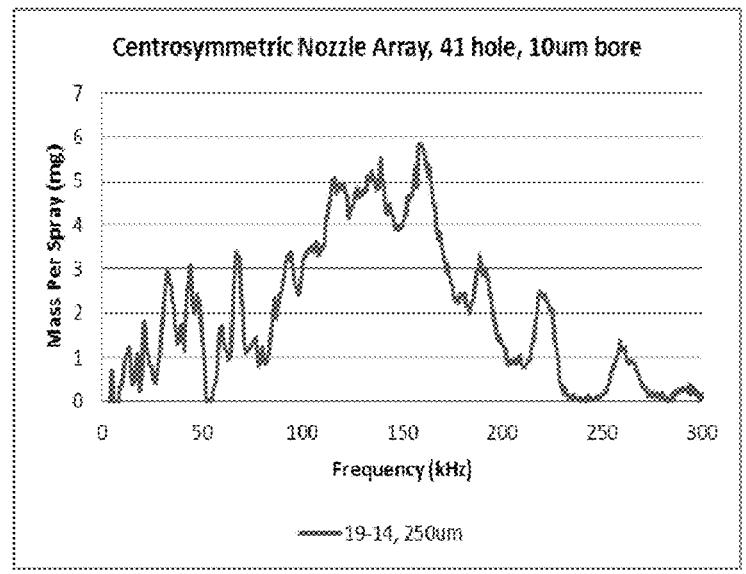
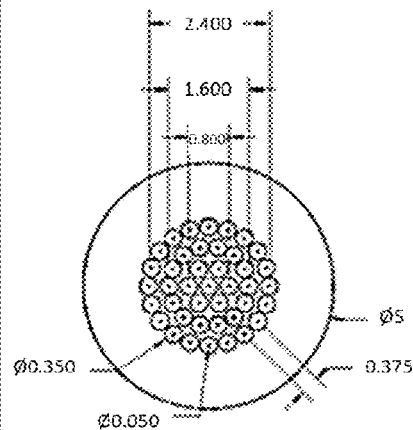
FIG. 20A
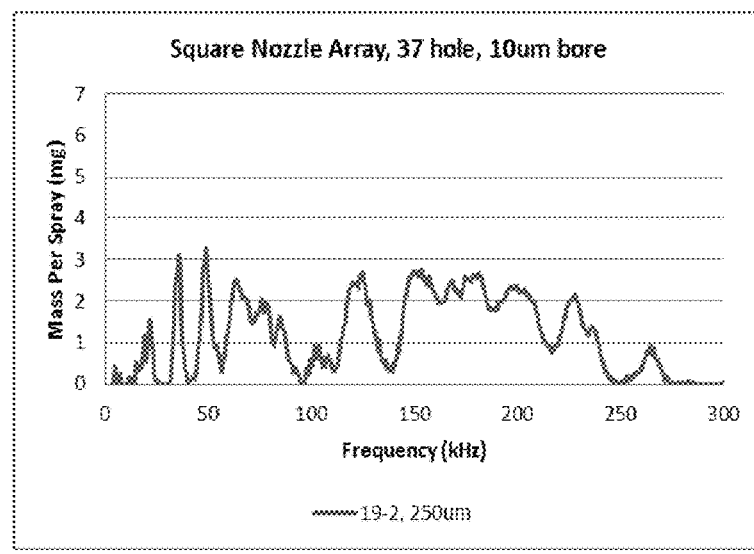
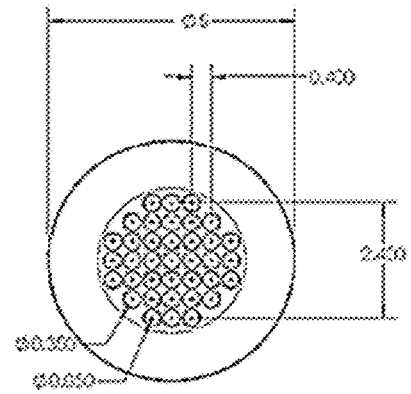
FIG. 20B

HIGH MODULUS POLYMERIC EJECTOR MECHANISM, EJECTOR DEVICE, AND METHODS OF USE

RELATED APPLICATIONS

This application claims the benefit of the filing date of U.S. Provisional Application No. 61/569,739, filed Dec. 12, 2011, and of U.S. Provisional Application No. 61/591,786, filed Jan. 27, 2012, contents of which are herein incorporated by reference in their entireties.

BACKGROUND OF THE INVENTION

Using spray devices to administer products in the form of mists or sprays is an area with large potential for safe, easy-to-use products. A major challenge in providing such a device is to provide consistent and accurate delivery of suitable doses.

An important area where spray devices are needed is in delivery of eye medications. The application of fluids, as in the case of eye drops, has always posed a problem, especially for children and animals who tend to blink or jerk at the critical moment of administration, causing the droplet to land on the eyelid, nose or other part of the face. The impact of a large drop or drops of fluid on the eyeball, especially when the fluid is at a different temperature, also tends to produce a blinking reaction. Elderly also often lose the hand coordination necessary to get the eye drops into their eyes. Stroke victims have similar difficulties. Dropper delivery often requires a particular physical position, such as tilting of the head or laying in a horizontal position, neither of which might be practical.

Often, it is important that the subject administer the correct dose the requisite number of times per day. However, in practice, subjects that are prescribed eye medications for home use tend to forget to dose, or dose excessively or cross-dose with other medications. One of the compliance problems is that, even if the subject is intent on following the treatment regimen, he or she may not be compliant for any number of reasons.

Currently, many of these medications are administered by eye droppers. Current eye drop devices often require either the head to be tilted back, the subject to lie down or provide downward traction on the lower eyelid, or a combination of traction and tilting, since the delivery mechanism typically relies on gravity for applying the medication. This is not only awkward, but involves a fair amount of coordination, flexibility and cooperation on the part of the subject to ensure that the medication gets into the eye while avoiding poking the eye with the dropper tip. Current eye dropper bottles pose the risk of poking the user in the eye, potentially causing physical damage to the eye, and further, exposing the tip to bacterial contamination due to contact with the eye. As such, the subject runs the risk of contaminating the medication in the eye drop bottle and subsequently infecting the eye. Additionally, a large volume of the medication flows out of the eye or is washed away by the tearing reflex. As a result, this method of administration is also inaccurate and wasteful. Moreover, the technology does not provide a satisfactory way of controlling the amount of medication that is dispensed, nor does it provide a way of ensuring that the medication that is dispensed actually lands on the eye and remains on the eye.

Eye droppers also provide no way of verifying compliance by a subject. Even if after a week of use the eye dropper bottle could be checked for the total volume of medication dispensed, e.g., by weighing the bottle, this does not provide a record of day-to-day compliance. A subject may have missed one or more doses and overdosed on other occasions. Also, the poor precision with which eye droppers deliver drops to the eye makes it difficult to determine whether the medication is actually delivered into the eye, even though it may have been dispensed.

Accordingly, there is a need for a delivery device that delivers safe, suitable, and repeatable dosages to a subject for ophthalmic, topical, oral, nasal, or pulmonary use.

SUMMARY OF THE INVENTION

The present disclosure includes an ejector device and method of delivering safe, suitable, and repeatable dosages to a subject for ophthalmic, topical, oral, nasal, or pulmonary use. The present disclosure also includes an ejector device and fluid delivery system capable of delivering a defined volume of fluid in the form of droplets having properties that afford adequate and repeatable high percentage deposition upon application.

The present disclosure includes and provides an ejector device for delivering a fluid to an eye of a subject, the device comprising a housing, a reservoir disposed within the housing for receiving a volume of fluid, and an ejector mechanism configured to eject a stream of droplets having an average ejected droplet diameter greater than 15 microns, with the stream of droplets having low entrained airflow such that the stream of droplets deposits on the eye of the subject during use.

The disclosure further includes and provides an ejector mechanism configured to eject a stream of droplets, the ejector mechanism comprising: an ejector plate coupled to a high modulus polymeric generator plate and a piezoelectric actuator; the high modulus polymeric generator plate including a plurality of openings formed through its thickness; and the piezoelectric actuator being operable to oscillate the ejector plate, and thereby the high modulus polymeric generator plate, at a frequency and generate a directed stream of droplets.

Another implementation of the disclosure provides a device for delivering a fluid to a target, the device comprising: a housing; a reservoir disposed within the housing for receiving a volume of fluid; and an ejector mechanism in fluid communication with the reservoir and configured to eject a stream of droplets, the ejector mechanism comprising an ejector plate coupled to a high modulus polymeric generator plate and a piezoelectric actuator. The high modulus polymeric generator plate includes a plurality of openings formed through its thickness; and the piezoelectric actuator is operable to oscillate the ejector plate, and thereby the high modulus polymeric generator plate, at a frequency and generate a directed stream of droplets.

In certain implementations, the ejector plate has a central open region aligned with the high modulus polymeric generator plate, and the piezoelectric actuator is coupled to a peripheral region of the ejector plate so as to not obstruct the plurality of openings of the high modulus polymeric generator plate. The plurality of openings of the high modulus polymeric generator plate may be disposed in a center region of the high modulus polymeric generator plate that is uncovered by the piezoelectric actuator and aligned with the central open region of the ejector plate. In certain implementations, the three-dimensional geometry and shape of the openings, including orifice diameter and capillary length, and spatial array on the high modulus polymeric generator plate may be controlled to optimize generation of the directed stream of droplets.

Another implementation includes a method for the fabrication of a high modulus polymeric generator plate for ejecting high viscosity fluids suitable for ophthalmic, topical, oral, nasal, or pulmonary use comprising laser micromachining of high modulus polymeric materials to form three-dimensional openings through the thickness of the material, the openings comprising a fluid entrance orifice, an entrance cavity, a capillary channel, and a fluid exit orifice, wherein the opening comprises an overall pitch length.

Yet another implementation of the disclosure includes and provides for a method of delivering a volume of ophthalmic fluid to an eye of a subject, the method comprising ejecting a directed stream of droplets of an ophthalmic fluid contained in a reservoir from openings of an ejector plate, the droplets in the directed stream having an average ejecting diameter in the range of 5-2500 microns, including but not limited to 20-400 microns, 20-200, 100-200, etc., and an average initial velocity in the range of 0.5-100 m/s, 1-100 m/s, including but not limited to, 2-20 m/s.

BRIEF DESCRIPTION OF THE DRAWINGS

FIG. 1A shows a cross-sectional view of an implementation of an ejector assembly.

FIG. 1C-2 shows a schematic top view of an implementation of an active region of a high modulus polymeric generator plate.

FIGS. 14A-14B illustrate exemplary generator plate structures according to an implementation of the disclosure.

FIG. 15A-15B illustrate a simulation of a pressure driven flow through in a capillary, according to implementations of the disclosure.

FIGS. 20A-20B illustrate spray performance as a function of opening placement on a generator plate, according to implementations of the disclosure.

DETAILED DESCRIPTION

Figure 1B:
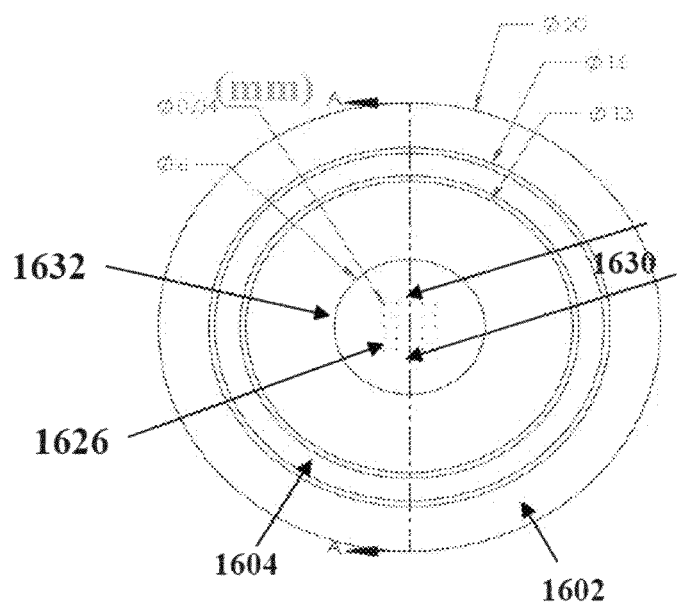
FIG. 1B shows a front view of an implementation of an ejector mechanism.

The present disclosure generally relates to ejector devices useful, e.g., in the delivery of fluid for ophthalmic, topical, oral, nasal, or pulmonary use, more particularly, for use in the delivery of ophthalmic fluid to the eye. In certain aspects, the ejector devices include an ejector assembly including an ejector mechanism which generates a controllable stream of droplets of fluid. Fluid includes, without limitation, suspensions or emulsions which have viscosities in a range capable of droplet formation using an ejector mechanism. Exemplary ejector devices and related methods useful in connection with the present disclosure are described in U.S. application Ser. No. 13/184,484, filed Jul. 15, 2011, entitled "Drop Generating Device", U.S. application Ser. No. 13/184,446, filed Jul. 15, 2011, entitled "Ophthalmic Drug Delivery" and U.S. application Ser. No. 13/184,468, filed Jul. 15, 2011, entitled "Method and System for Performing Remote Treatment and Monitoring", which applications are each herein incorporated by reference in their entireties.

As discussed further herein, the generation of droplets using ejector devices of the disclosure depends on a complex interaction between liquid flow through micro-orifices, fluid-surface interactions, exit orifice diameter, entrant cavity geometry, film thickness, capillary tube length, film mechanical properties, amplitude and phase of mechanical displacement, frequency of displacement, etc. Moreover fluid properties such as viscosity, density, and surface energy play major roles in droplet generation. In accordance with certain aspects of the disclosure, ejector mechanism structures and generator plate opening geometries that optimize droplet generation dynamics and microfluidic flow are disclosed.

As explained in further detail herein, in accordance with certain aspects of the present disclosure, the ejector mechanism may form a directed stream of droplets which may be directed toward a target. The droplets may be formed in a distribution of sizes, each distribution having an average droplet size. The average droplet size may be in the range of about 15 microns to over 400 microns, greater than 20 microns to about 400 microns, about 20 microns to about 80 microns, about 25 microns to about 75 microns, about 30 microns to about 60 microns, about 35 microns to about 55 microns, about 20 microns to about 200 microns, about 100 microns to about 200 microns, etc. However, the average droplet size may be as large as 2500 microns, depending on the intended application. Further, the droplets may have an average initial velocity of about 0.5 m/s to about 100 m/s, e.g., about 0.5 m/s to about 20 m/s, about 0.5 to about 10 m/s, about 1 m/s to about 5 m/s, about 1 m/s to about 4 m/s, about 2 m/s, etc. As used herein, the ejecting size and the initial velocity are the size and initial velocity of the droplets when the droplets leave the ejector plate. The stream of droplets directed at a target will result in deposition of a percentage of the mass of the droplets including their composition onto the target.

As described herein, the ejector device and ejector mechanism of the disclosure may be configured to eject a fluid of generally low to relatively high viscosity as a stream of droplets. By way of example, fluids suitable for use by the ejector device can have very low viscosities, e.g., as with water at 1 cP, or less, e.g. 0.3 cP. The fluid may additionally have viscosities in ranges up to 600 cP. More particularly, the fluid may have a viscosity range of about 0.3 to 100 cP, 0.3 to 50 cP, 0.3 to 30 cP, 1 cP to 53 cP, etc. In some implementations, the ejection device may be used to eject a fluid having a relatively high viscosity as a stream of droplets, e.g., a fluid having a viscosity above 1 cP, ranging from about 1 cP to about 600 cP, about 1 cP to about 200 cP, about 1 cP to about 100 cP, about 10 cP to about 100 cP, etc. In some implementations, solutions or medications having the suitable viscosities and surface tensions can be directly used in the reservoir without modification. In other implementations, additional materials may be added to adjust the fluid parameter. By way of example, exemplary fluids are illustrated below:

| drugs/fluids | dynamic viscosity (cP) | kinematic viscosity (cP) | density |
|---|---|---|---|
| water | 1.017 | 1.019 | 0.99821 |
| Xalatan ™ | 1.051 | 1.043 | 1.00804 |
| Tropicamide | 1.058 | 1.052 | 1.00551 |
| Restasis ™ | 18.08 | 17.98 | 1.00535 |

Viscosity measured at 20° C.

Droplets may be formed by an ejector mechanism from fluid contained in a reservoir coupled to the ejector mechanism. The ejector mechanism and reservoir may be disposable or reusable, and the components may be packaged in a housing. The housing may be disposable or reusable. The housing may be handheld, miniaturized, or formed to couple to a base, and may be adapted for communication with other devices. Housings may be color-coded or configured for easy identification. Ejector devices, in some implementations, may include illumination means, alignment means, temperature control means, diagnostic means, or other features. Other implementations may be part of a larger network of interconnected and interacting devices used for subject care and treatment. The ejector mechanism may be, e.g., a piezoelectric actuator as described herein.

Figure 1C:
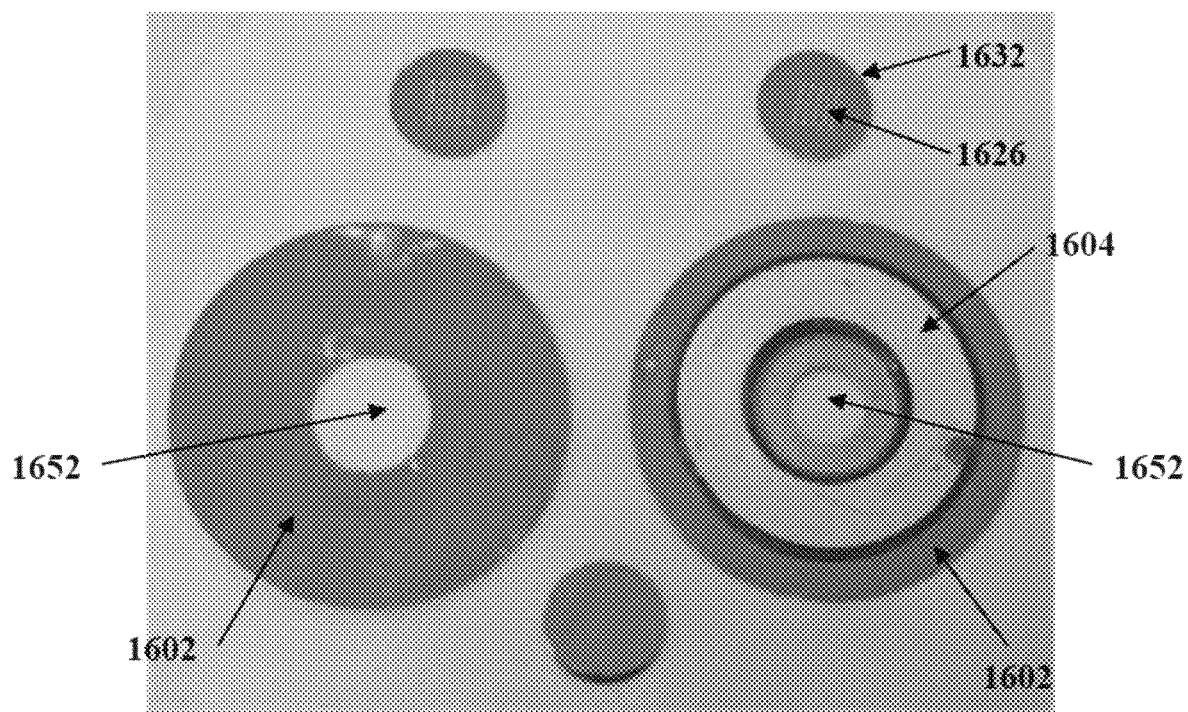
FIG. 1C shows an exploded view of an implementation of an ejector mechanism.

As discussed herein, in certain aspects, the ejector mechanism may be piezoelectric. Referring to FIGS. 1A-C, an ejector assembly 1600 may include an ejector mechanism 1601 and reservoir 1620. The ejector mechanism 1601 may include an ejector plate 1602 coupled to a high modulus polymeric generator plate 1632 including one or more openings 1626, that can be activated by a piezoelectric actuator 1604 which vibrates to deliver a fluid 1610, contained in a reservoir 1620, in the form of ejected droplets 1612 along a direction 1614. Again, the fluid may be an ophthalmic fluid that is ejected towards an eye 1616 of a human adult, child, or animal. Additionally, the fluid may contain an active pharmaceutical to treat a discomfort, condition, or disease of a human or an animal.

As shown in FIG. 1A, ejector plate 1602 is disposed over reservoir 1620 which contains fluid 1610. Surface 1625 of ejector plate 1602 is adjacent to the fluid 1610. Reservoir 1620 has open region 1638 which is adjacent to surface 1625 and to openings 1626. In this implementation, surface 1625 encloses the fluid 1610 in the reservoir 1620. The reservoir 1620 may be coupled to the ejector plate 1602 at a peripheral region 1646 of the surface 1625 of the ejector plate 1602 using a suitable seal or coupling. By way of example, the reservoir 1620 may be coupled via an O-ring 1648a. Although not shown, more than one O-ring can be used. As known in the art, the O-rings may have any suitable cross-sectional shape. Furthermore, other couplers such as polymeric, ceramic, or metallic seals can be used. Alternatively, the coupling can be eliminated altogether and reservoir 1620 may be integrally connected to ejector plate 1602, for example by welding or over molding. In such an implementation, an opening through which fluid is supplied to reservoir 1620 may be provided (not shown). Further still, the couplings may be made removable, such as a hinge, or may be made flexible or nonrigid connector, e.g., polymeric connector.

Other than the open region 1638, portions of the ejector plate 1602 may be covered by an additional reservoir wall 1650. In the implementation of FIG. 1A, wall 1650 does not directly contact the ejector plate 1602, rather it is coupled to O-rings 1648a. Alternatively, wall 1650 can be directly attached to ejector plate 1602. Furthermore, reservoir 1620 can be directly attached to ejector plate 1602 and wall 1650 can be omitted altogether.

The configuration of the reservoir 1620, including the shape and dimension, can be selected based on the amount of fluid 1610 to be stored, as well as the geometry of the ejector plate 1602. Alternative forms of reservoirs include gravity-fed, wicking, or collapsible bladders which operate under pressure differentials. These reservoirs may be pre-filled, filled using a micro-pump or by replacement of a cartridge. The micro pump may fill the reservoir by pumping fluid into or out of a collapsible or noncollapsible container. The cartridge may include a container which is loaded into the reservoir. Alternatively, the cartridge itself may be coupled to a disposable ejector assembly which is then replaced within the housing after a specified number of discharges. Exemplary reservoirs are illustrated in U.S. patent application Ser. No. 13/184,484, filed Jul. 15, 2011, the contents of which are herein incorporated by reference.

In some implementations, the reservoir 1620 includes through holes 1642 (only one shown in FIG. 1A) to allow air to escape from or enter the reservoir 1620 and keep the fluid 1610 in the reservoir at the appropriate ambient pressure. The through holes 1642 have a small diameter so that the fluid 1610 does not leak from the holes. Alternatively, no openings may be formed in the reservoir 1620, and at least a portion, e.g., the portion 1644, or the entire reservoir 1620 can be collapsible, e.g., in the form of a bladder. The entire reservoir may also be made in the form of a flexible or collapsible bladder. Accordingly, as the fluid 1610 is ejected through openings 1626, the reservoir 1620 changes its shape and volume to follow the changes in the amount of fluid 1610 in the reservoir 1620.

In the implementation of FIG. 1A, the ejector mechanism 1601 is activated by being vibrated by piezoelectric actuator 1604. Two electrodes 1606a and 1606b are formed on two opposite surfaces 1634 and 1636 of the piezoelectric actuator 1604 that are parallel to the surface 1622 of the ejector plate 1602 and activate the piezoelectric actuator 1604 to vibrate the ejector plate 1602 and a high modulus polymeric generator plate 1632 (described in further detail herein). The electrodes 1606a and 1606b can be attached to the ejector plate or piezoelectric actuator in any known manner including fixing by adhesive or otherwise bonding. They may also be overmolded in place to ejector plate 1602. Wires or other conductive connectors can be used to affect necessary electrical contact between ejector plate 1602 and the electrodes 1606a and 1606b. Alternatively, the electrodes may be formed on the ejector plate 1602 by plating or otherwise depositing. By way of example, the electrodes are attached by adhesive 1628 which is applied between the electrode 1606a and the ejector plate 1602. Electrode 1606a is in electrical contact with ejector plate 1602. When a voltage is applied across the electrodes 1606a and 1606b, the piezoelectric actuator 1604 deflects ejector plate 1602 and likewise high modulus polymeric generator plate 1632 to change shape to be more concave or convex.

An extensive range of voltages corresponding to different piezoelectric materials are known in the art, but by way of example, a voltage differential of between 5 and 60 V, 30 and 60 V, e.g., 40 or 60 V may be applied to the electrodes. When the direction of the voltage differential is reversed, for example to −40 or −60, the plate will deflect in the opposite direction. In this way, the piezoelectric actuator 1604 causes oscillation of ejector plate 1602 and high modulus polymeric generator plate 1632 which constitutes the vibration that results in formation of the droplets 1612 from fluid 1610. As the alternating voltage is applied to electrodes 1606a and 1606b, the ejector plate 1602 and the high modulus polymeric generator plate 1632 oscillate, causing the fluid droplets 1612 to accumulate in the openings 1626 and eventually be ejected from the openings 1626 along the direction 1614 away from the reservoir 1620. The frequency and wavelength of oscillation may depend on many factors, including but not limited to, the thickness, composition and morphology and mechanical properties of the ejector plate 1602, the volume of the openings 1626, the number of openings 1626, composition and structure of the piezoelectric actuator 1604, piezoelectric actuation driving voltage, frequency and waveform, the viscosity of the fluid, the stiffness of the ejector plate 1602, properties of the high modulus polymeric generator plate 1632, temperature and other factors. These parameters may be adjusted or selected to create the desired droplet stream. The frequency of droplet ejection also depends on many factors. In some implementations, the droplets 1612 are ejected at a frequency lower than the pulse frequency to the piezoelectric actuator 1604. For example, the droplets 1612 are ejected every 1-1000 cycles, and more specifically 8-12 cycles, of the ejector plate/high modulus polymeric generator plate vibration.

Without intending to be limited by theory, piezoelectric actuated generator plates possess a large number of eigenmodes that define the shape that the generator plate assumes when in motion, and the optimum eigenmode and shape provides the maximum displacement over the generator plate's active area. Exciting a given eigenmode requires placing the piezoelectric actuator at a given location relative to the standing wave of the generator plate. In this regard, the size and shape of a piezoelectric actuator, e.g., thickness, outer dimension and inner dimension, may determine, at least in part, its placement relative to the generator plate. Further, placement and bonding of the piezoelectric actuator on the generator plate may increase the generator plate stiffness. However, movement of the portion of the generator plate inside the inner dimension of the piezoelectric actuator is generally not restricted by placement of piezoelectric actuator.

In accordance with certain aspects of the disclosure, with reference to FIGS. 1B-1C, a first surface 1622 of ejector plate 1602 may be coupled to high modulus polymeric generator plate 1632. The ejector plate 1602 may generally comprise a central open region 1652 configured to align with the high modulus polymeric generator plate 1632. The high modulus polymeric generator plate 1632 may then be coupled with the ejector plate 1602 such that a center region 1630 of the high modulus polymeric generator plate 1632 aligns with the central open region 1652 of the ejector plate 1602. The center region 1630 of the high modulus polymeric generator plate 1632 may generally include one or more openings 1626, and alignment of the central open region 1652 of the ejector plate 1602 and the center region 1630 of the high modulus polymeric generator plate 1632 including the one or more openings 1626 allows for through communication of the one or more openings 1626.

In certain aspects, the central open region 1652 of the ejector plate 1602 may be smaller than the high modulus polymeric generator plate 1632 to provide sufficient overlap of material so as to allow for coupling of the ejector plate 1602 and the high modulus polymeric generator plate 1632. However, the central open region 1652 of the ejector plate 1602 should, in certain embodiments, be sized and shaped so as to not interfere with or obstruct the center region 1630 (and thereby one or more openings 1626) of the high modulus polymeric generator plate 1632.

By way of non-limiting example, the central open region 1652 of the ejector plate may be shaped in a manner similar to the high modulus polymeric generator plate 1632, and may be sized so as to have, e.g., about 0.5 mm to about 4 mm, about 1 mm to about 4 mm, about 1 mm to about 2 mm, etc., of overlap material available for coupling of the high modulus polymeric generator plate 1632 to the ejector plate 1602 (e.g., overlap on all sides). For instance, the central open region 1652 of the ejector plate may be shaped as a square, a rectangle, a circle, an oval, etc., in a manner to generally match the shape of the high modulus polymeric generator plate 1632, and sized such that the central open region 1652 is, e.g., about 0.5 mm to about 4 mm smaller in overall dimensions (i.e., the diameter of a circle is about 0.5 to about 4 mm smaller, the major and minor axes of an oval are about 0.5 to about 4 mm smaller, the length of the sides of a square or rectangle are about 0.5 to about 4 mm smaller, etc.)

In certain embodiments, the high modulus polymer generator plate may be sized and shaped so as to have an overall outer dimension (OD) of about 4 mm to about 8 mm, e.g., 4 mm, 5 mm, 6 mm, etc. The ejector plate may be sized and shaped so as to have an overall outer dimension (OD) of about 18 mm to about 24 mm, e.g., 20 mm, 21 mm, 22 mm, 23 mm, etc., and an inner dimension (ID) (i.e., of the central opening) configured to provide sufficient overlap with the OD of the generator place. For instance, the ID of the ejector plate may be about 3 mm to about 16 mm, e.g., 4 mm, 6 mm, 12 mm, 14 mm, 16 mm, etc.

High modulus polymeric generator plate 1632 may be coupled to ejector plate 1602 using any suitable manner known in the art, depending on the materials in use. Exemplary coupling methods include use of adhesive and bonding materials, e.g., glues, epoxies, bonding agents, and adhesives such as loctite E-30CL or Loctite 480 or 380 epoxies or other suitable super glue such as Loctite ultra gel, welding and bonding processing, e.g., ultrasonic or thermosonic bonding, thermal bonding, diffusion bonding, laser welding or press-fit etc.

Surface 1622 of ejector plate 1602 may be coupled to a piezoelectric actuator 1604, which activates high modulus polymeric generator plate 1632 to form the droplets upon activation. The manner and location of attachment of the piezoelectric actuator 1604 to the ejector plate 1602 affects the operation of the ejector assembly 1600 and the creation of the droplet stream. In the implementation of FIGS. 1B-C, the piezoelectric actuator 1604 may be coupled to a peripheral region of surface 1622 of plate 1602, while high modulus polymeric generator plate 1632 is coupled to surface 1622 so as to align with central open region 1652 of ejector plate 1602, as described above. Piezoelectric actuator 1604 is generally coupled to ejector plate 1602 so as to not cover or obstruct center region 1630 (and thereby one or more openings 1626) of the high modulus polymeric generator plate 1632. In this manner, fluid 1610 may pass through openings 1626 to form droplets 1612. In certain embodiments, the piezoelectric actuator may be shaped to generally correspond in shape with the generator plate. By way of example, the piezoelectric actuator may be sized to have an overall outer dimension (OD) of about 8 mm to about 24 mm, e.g., 8 mm, 10 mm, 12 mm, 14 mm, 16 mm, 18 mm, 19 mm, 20 mm, 21 mm, 22 mm, etc., and an inner dimension (ID) of about 4 mm to about 18 mm, e.g., 4 mm, 10 mm, 12 mm, 13 mm, 14 mm, 15 mm, 16 mm, etc.

As the ejector assembly 1600 is used for delivering therapeutic agents or other fluids to the desired target, e.g., the eye, the ejector assembly 1600 may be generally designed to prevent the fluid 1610 contained in the reservoir 1620 and the ejected droplets 1612 from being contaminated. In some implementations, for example, a coating (not shown) may be formed over at least a portion of the exposed surface(s) of the piezoelectric actuator 1604, the ejector plate 1602, the high modulus polymeric generator plate 1632, etc. The coating may be used to prevent direct contact of the piezoelectric actuator 1604 and the electrodes 1606a and 1606b with the fluid 1610. The coating may be used to prevent interaction of the ejector plate 1602 or high modulus polymeric generator plate 1632 with the fluid, or it may be used to protect the piezoelectric actuator 1604 and electrodes 1606a and 1606b from the environment. For example, the coating can be a conformal coating including a nonreactive material, e.g., polymers including polyamide imide (PAI), polyether ether ketone (PEEK), polypropylene (PP), or high density polyethylene (HDPE), or an inert material selected from the group consisting of gold (Au), platinum (Pt), palladium (Pd), titanium nitride (TiN), chromium nitride (CrN), diamond like carbon/amorphous carbon, chromium carbon nitride, and aluminum (Al). Coatings are described in further detail herein.

The high modulus polymeric generator plate 1632 may be a perforated plate that contains at least one opening 1626. The one or more openings 1626 form the droplets as fluid 1610 is passed through. The high modulus polymeric generator plate 1632 may include any suitable configuration of openings, one configuration being depicted in FIG. 1B. By way of example, the openings may be formed as a grid, a spiral, or in a rectangular, rectilinear, or other pattern. The pattern may be regular or irregular. The pattern may maintain a uniform spacing of openings, or the spacing may be varied. For example, the density of openings may increase or decrease towards the center of the plate. The pattern may also cover all or part of the plate, i.e., center region 1632 may cover all or part of the high modulus polymeric generator plate, etc.

The openings 1626 may be formed through the thickness of the high modulus polymeric generator plate 1632 in any suitable three-dimensional geometry, shape or volume, including orifice diameter and capillary length, and spatial array on the high modulus polymeric generator plate. The formation and arrangement of the openings may be controlled so as to optimize generation of the directed stream of droplets. Further, the openings may be formed with an appropriate aspect ratio (i.e., height/thickness of opening vs. diameter of opening) selected and configured to efficiently eject droplets based, at least in part, on fluid properties.

Without being limited by theory, higher aspect ratio openings produce a higher pressure gradient in the fluid being ejected, and therefore may be generally preferred for higher viscosity fluids. By way of example, in certain implementations, the high modulus polymeric generator plates may have openings with aspect ratios between about 1 and about 10, about 1 and about 5, about 1 and about 4, etc. Such aspect ratios may be obtained by varying opening height/thickness (i.e., high modulus polymeric generator plate thickness) and opening diameter. By way of example, opening diameter may range from about 20 μm to about 100 μm, about 20 μm to about 80 μm, about 20 μm to about 50 μm, about 30 μm to about 40 μm, etc. Opening height/thickness (i.e., high modulus polymeric generator plate thickness) may range from about 50 μm to about 500 μm, about 100 μm to about 200 μm, about 150 μm to about 200 μm, about 160 μm, etc. Selection of the aspect ratio of the openings may allow for formation of droplets of fluids having relatively high viscosities.

In certain implementations, the openings may have a generally cylindrical shape, that is, the diameter of the opening extending from surface 1622a of high modulus polymeric generator plate 1632 to surface 1625a of high modulus polymeric generator plate 1632 remains generally constant. Nevertheless, the openings need not be limited to this cylindrical shape and may be fluted, tapered, conical, oval, hourglass, etc. In other implementations, the openings may comprise a general entrance cavity region (e.g., a cylindrical, fluted, tapered, conical, hour glass, etc., shaped cavity region) leading to a capillary channel and exit orifice. See, e.g., FIGS. 1D-K. By way of example, a tapered opening may extend the entire thickness from surface 1622a to 1625a, or it may extend partway with a capillary channel extending to an exit orifice. The opening may also be beveled on one or both sides. The bevel may have an angled edge or a curved edge. The cross section of the opening may be round, or may have any other suitable shape. A few examples may be round, oval, rectangular or polygonal. The openings may be regularly shaped or irregularly shaped. The shape may be symmetric or asymmetric. The shape and aspect ratio of the openings may impact ejection of droplets, and may be optimized so as to efficiently eject fluids of varying viscosities, etc. In an exemplary implementation of FIG. 1L, the openings 1626 may comprise a fluid entrance orifice 1626a, an entrance cavity 1626b, a capillary channel 1626c, and a fluid exit orifice 1626d, wherein the opening comprises an overall pitch length 1626e.

As indicated herein, the size, shape, and aspect ratio of the openings 1626 affect the size and shape of the droplets and the droplet stream created by the ejector mechanism 1601. It may also affect the density distribution throughout the droplet stream. Thus, the size, shape, and aspect ratio of the openings as well as their pattern may be selected and configured to produce the desired properties of the droplet stream, based in part on fluid properties, in accordance with certain aspects of the present disclosure.

Figures 1, 1C, 2:
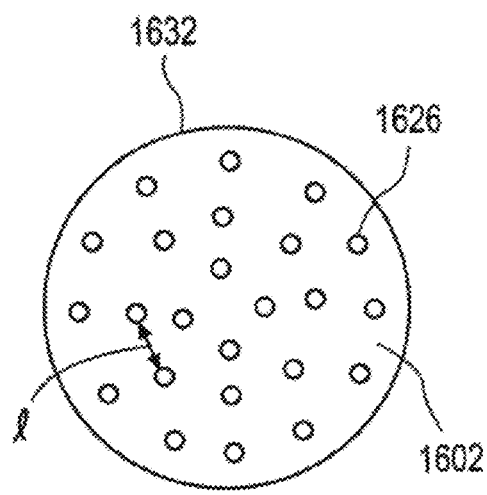
Figure 1D:
FIGS. 1D-1K show partial cross-sectional views showing examples of high modulus polymeric generator plate configurations.
Figure 1E:
Figure 1F:
Figure 1G:
Figure 1H:
Figure 1I:
Figure 1J:
Figure 1K:
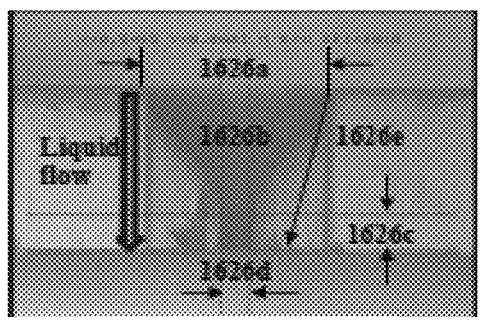
Figure 2A:
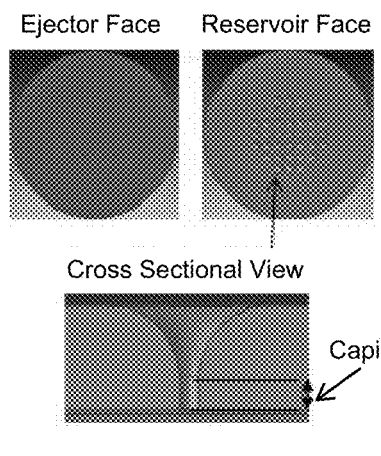
FIGS. 2A-2F illustrate exemplary CAD implementations and laser micromachined high modulus polymeric generator plate configurations, top and bottom views, and cross-sectional views of related generator plates and openings, according to certain implementations of the disclosure.
Figure 2B:
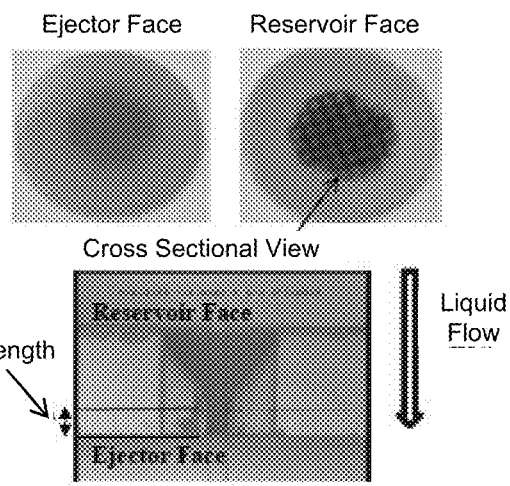
Figure 2C:
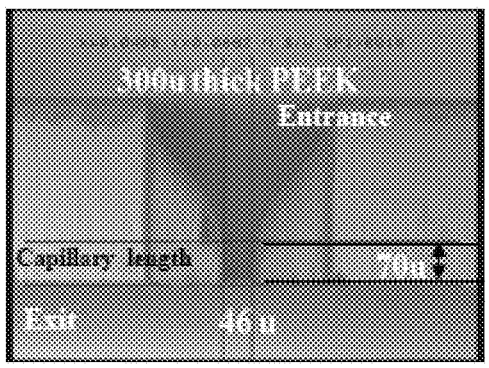
Figure 2D:
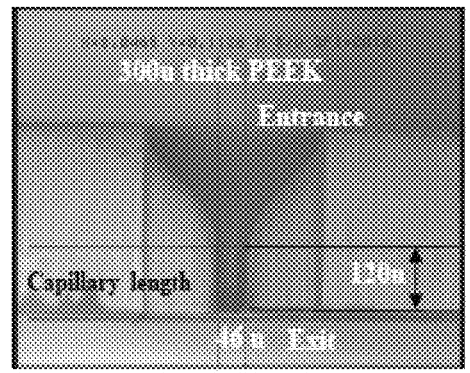
Figure 2E:
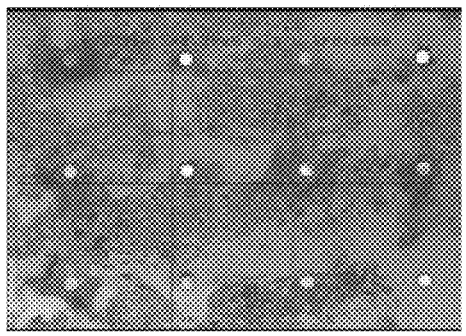
Figure 2F:
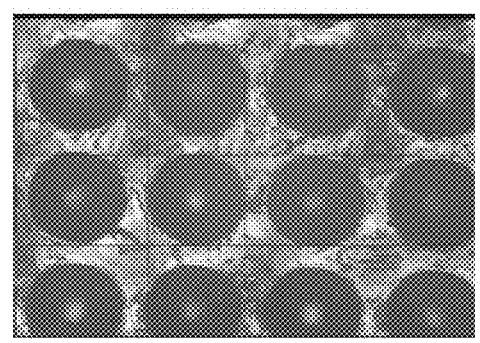

As with the size and shape of the openings 1626, the size and shape of the central region 1630 can be selected based on the desired properties of the droplet stream. As shown in FIG. 1C-2, by way of example, the openings 1626 are arranged in a circular pattern in the active region of high modulus polymeric generator plate 1632, but other patterns may also be used as explained above. The distance 1 between adjacent openings 1626 may be any suitable value, including 1 micron to a few mm, e.g., 150 microns to 300 microns. In one particular implementation, 1 is chosen to be 200 microns. Additionally, also as explained above, the separation of the openings 1626 need not be uniform.

Again, droplet stream generation depends on a complex interaction between fluid flow through openings, aspect ratios of openings, exit and entrance orifice diameter, entrance cavity geometry, capillary channel length, generator plate material composition and mechanical properties, amplitude and phase of generator plate displacement, frequency of displacement of generator plate, and fluid properties such as viscosity, density, and surface energy, for example. For instance, without intending to be limited by theory, fluid flow rate in microchannels and capillary channels is dependent on the pressure difference between the capillary channel and exit face as described by the Young-LaPlace equation, divided by the resistance of the fluid flow within the capillary channel. As such, the three-dimensional geometry of the capillary channel and orifice diameters of the openings of the generator plate can impact fluid flow rates through the openings.

| Flow rate | Fluid Resistance | Young-LaPlace equation |
|---|---|---|
| $Q = \Delta P/R$ | $R = \dfrac{8\mu L}{\pi r_1^4}$ | $\Delta P = \gamma\left(\dfrac{1}{r1} + \dfrac{1}{r2}\right)$ |
| | $\mu$ = Fluid viscosity<br>L = Capillary lenght<br>r1 = Capillary radius | $\gamma$ = Fluid surface tension<br>r1 = Capillary radius<br>r2 = Flute radius |

The velocity of the fluid is thus:

$$V(r) = \frac{\pi \Delta p A_{in} \rho_{in}}{8 \mu l A_{out} \rho_{out}} (R^2 - r^2)$$

where R is the diameter of the channel and r is the volume of fluid within the channel.

In some implementations, the length of the capillary channel may be selected so as to optimize flow and ejected mass of fluid forming the droplet stream. By way of example, capillary channels may range from 0 μm to about 150 μm, about 70 μm to about 150 μm, about 70 μm to about 120 μm, etc. In certain implementations, the capillary channel may be between 120 μm and 150 μm, particularly for high viscosity fluids.

In some implementations, the ejector plate 1602 may be formed of a metal, e.g., stainless steel, nickel, cobalt, titanium, iridium, platinum, or palladium or alloys thereof. Alternatively, the plate can be formed of suitable material, including other metals or polymers, such as polyether ether ketone (PEEK) or talc-filled PEEK, and be coated as described herein. The plate may be a composite of one or more materials or layers. The plate may be fabricated for example by cutting from sheet metal, pre-forming, rolling, casting, photoetching, laser cutting or otherwise shaping. The coatings may also be deposited by suitable deposition techniques such as sputtering, vapor deposition including physical vapor deposition (PAD), chemical vapor deposition (COD), or electrostatic powder deposition. The protective coating may have a thickness of about less than 0.1 μm to about 500 μm. It is desirable that the coating adhere to the ejector plate 1602 sufficiently to prevent delamination when vibrating at a high frequency.

Referring to FIGS. 1B-C, in one implementation, the ejector plate 1602 and high modulus polymeric generator plate 1632 may have concentric circular shapes. In certain aspects, the ejector plate may be larger than the high modulus polymeric generator plate, so as to accommodate coupling of the high modulus polymeric generator plate and other components (e.g., piezoelectric actuator, etc.) described herein. Likewise, in certain implementations, the high modulus polymeric generator plate 1632 may have a reduced size or diameter (in the implementation of a circular configuration) relative to the ejector plate 1602. In certain aspects, the overall size or diameter of high modulus polymeric generator plate 1632 may be, at least in part, determined by the size of center region 1630 and by the arrangement of openings 1626.

However, both plates may independently have other shapes, e.g., an oval, square, rectangular, or generally polygonal shape, and may be the same or different. Overall size and shape may be any suitable size and shape, and may be selected based on ejector device design parameters, e.g., size and shape of an outer device housing, etc. Additionally, the plates need not be flat, and may include a surface curvature making it concave or convex. The piezoelectric actuator 1604 may be of any suitable shape or material. For example, the actuator may have a circular, oval, square, rectangular, or a generally polygonal shape. The actuator 1604 may conform to the shape of the ejector plate 1602, high modulus polymeric generator plate 1632, or regions 1630/1652. Alternatively, the actuator 1604 may have a different shape. Furthermore, the actuator 1604 may be coupled to the ejector plate 1602 or surface 1622 of the ejector plate 1602 in one or more sections. In the example shown in FIGS. 1B-C, the piezoelectric actuator 1604 is illustrated in the shape of a ring that is concentric to the ejector plate 1602, high modulus polymeric generator plate 1632, and regions 1630/1652.

In some implementations, the high modulus polymeric generator plate 1632 may be formed from any suitable polymeric material having a modulus of elasticity suitable to provide sufficient tensile strength and flexibility to allow fabrication of the one or more openings as well as vibration by the piezoelectric actuator during use. Such materials may generally include those with a modulus above about 100,000 psi, between about 100,000 psi and about 700,000 psi, etc. (e.g., high modulus polymeric materials). Exemplary materials include, ultrahigh molecular weight polyethylene (UHMWPE), polyimide (Kapton™), polyether ether ketone (PEEK), talc-filled PEEK, polyvinylidine fluoride (PVDF, Kynar™), polyetherimide (Ultem™), and be coated as discussed herein.

By way of example, suitable materials include:

| Material | Modulus Tensile (psi) | Modulus Flexural (psi) | Seal/Bond | Coated (1 or 2 side) | Melt Degrees F./C. | Thickness (um) | FDA Compliant/ Approved |
|---|---|---|---|---|---|---|---|
| UHMWPE | 105,000 | | Fusion Weld/Heat Seal | Treatable | 273/134 | 76 | FDA & USDA Approved |
| Kynar ™, Solef (Polyvinylidine Fluoride) | 250,000 | 260,000 | Fusion Weld | Treatable | 329-338 (165-170) | | Resin FDA Compliant |
| Kapton (polyimide) | ~350,000 | | 652 F 20 PSI 20 Sec | 1 or 2 | N/A | 25, 50, 76, 127 | FDA Certified Grade |
| PEEK (polyether ether ketone | 390,000 | 530,000 | Si Adhesive/ Mechanical | Treatable | 644/340 | 76 | FDA Certified Grade |
| Ultem ™ (polyetherimide) | 475,000 | 480,000 | Heat Seal | Treatable | 420/216 | 76 | Resin FDA Compliant |

The high modulus polymeric generator plate may be a composite of one or more materials or layers. The openings in the plate may be formed using suitable methods including but not limited to drilling by mechanical or thermal stamping or optical means, such as laser drilling or ablation. More particularly, in certain implementations, the openings may be formed via laser machining. Without being limited, laser machining of polymeric materials provides an efficient means of fabricating the high modulus polymeric generator plate described herein by offering accurate control of the three-dimensional geometry and spatial array of openings. Exemplary laser micromachining technology may utilize high power lasers, such as Excimer lasers, to ablate polymeric materials, for example, while under computer control. The manipulation of laser position, pulse duration and power provides for accurate three-dimensional structuring of openings. Exemplary methods for laser micromachining and ablation are disclosed, e.g., in U.S. Pat. Nos. 5,296,673, 4,414,059, and Andreas Ostendorfa, et al., *Proceedings of SPIE* Vol. 4633 (2002), 128-135, the contents of which are herein incorporated by reference.

In one implementation, laser micromachining and UV-laser-assisted micromachining of polymeric materials may be used to form a high modulus polymer generator plate of this disclosure. In certain aspects, polymeric materials, such as polyether ether ketone (PEEK), talc-filled PEEK, polysulfone (PSU) and polyimide (PI) may be selected, due in part to their chemical stability and corresponding absorbance with KrF-Excimer laser radiation (wavelength 248 nm) as well as frequency quadrupled (4ω) Nd:YAG laser radiation (wavelength 266 nm). Patterns and complex shapes may be formed on masks projected onto the target material to ablate patterns onto the target and to obtain the desired pattern. The projected mask pattern may be linearly demagnified from the mask through a lens and onto the target for ablation, for example, to obtain resolutions from 1 to 10 microns, e.g., 2 microns. Direct optical imaging of complex structures may also be formed on masks and allows use of motorized masks, which in turn provides a means of rotating masks and which further enables complex mask structures to be changed with high precision and without stopping the ablation process.

Figure 12A:
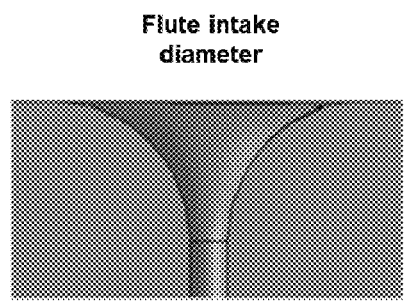
FIGS. 12A-12D illustrate exemplary CAD implementations and laser micromachined high modulus polymeric generator plate configurations, top and bottom views, and cross-sectional views of related generator plates and openings, according to certain implementations of the disclosure.
Figure 12B:
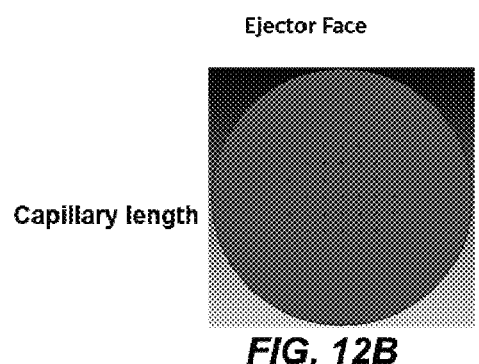
Figure 12C:
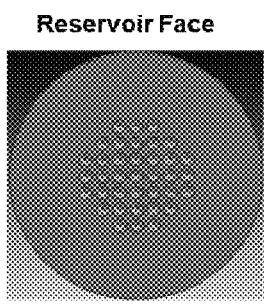
Figure 12D:
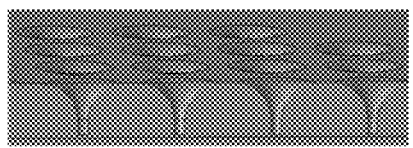

In certain implementations, a computer aided design (CAD) drawing may be used to design a mask used to control the spatial distribution of a generator plate array and to fabricate the internal three-dimensional geometry of the opening orifices. By way of non-limiting example, FIGS. 2A-2F and FIG. 12A-12D illustrate an exemplary CAD drawing of generator plate desired opening geometries, and corresponding generator plates and openings. Top and bottom views, as well as cross-sectional views are illustrated with openings having varying capillary channel lengths (e.g., FIGS. 2C and 2D). As shown, the openings may comprise a fluid entrance orifice, an entrance cavity, a capillary channel, and a fluid exit orifice. The entrance and exit sides of the generator plate are separately illustrated in FIGS. 2E and 2F. With reference to FIG. 12, FIGS. 12A and 12D illustrate exemplary fluted openings of a generator plate, and FIGS. 12B-12C illustrate the entrance and exit sides of a generator plate. Such an exemplary CAD configuration may be used to design a mask and for computer control of micromachining process.

This mask technique may be further used for patterning large complex structures. CAD data may also be used to control the laser beam by beam shaping using cylindrical lenses and thereby to control the machined three-dimensional structure by controlling the laser fluence at the target to control the removal of photodecomposition products by ablation. Control of ambient environment through use of oxygen purge promotes formation of volatile photo-degradation products such as $CO_2$, CO, etc. Furthermore, curved grooves and grooves with a variation of cross section may be fabricated using this process. By way of non-limiting example, with reference to FIG. 1K, the CAD drawing may be comprised of an opening with an entrance diameter of about 300 μm, capillary channel length of about 70 μm to about 120 μm, exit orifice of about 40 μm to 50 μm, e.g., 46 μm, and overall pitch of about 400 μm pitch.

Figure 8:
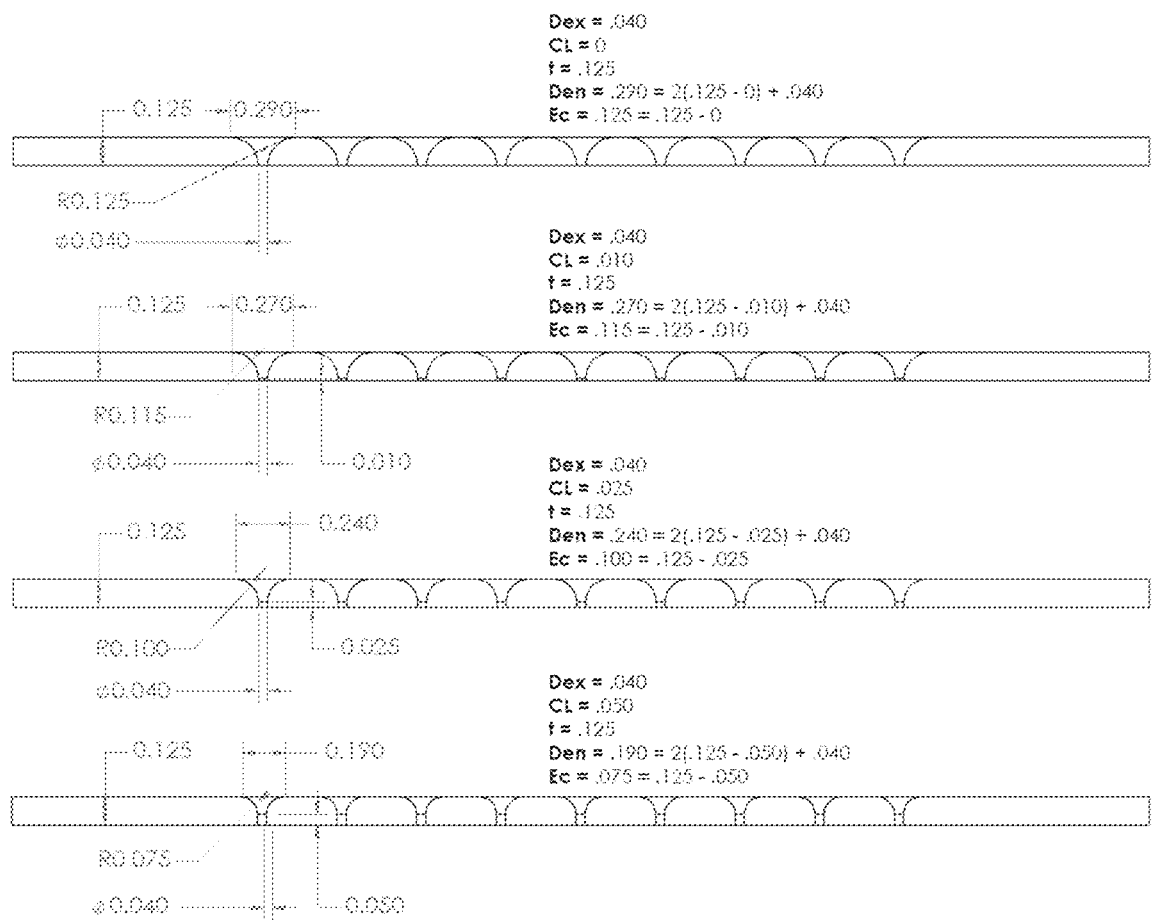
FIG. 8 illustrates exemplary generator plate structures according to an implementation of the disclosure.
Figure 9:
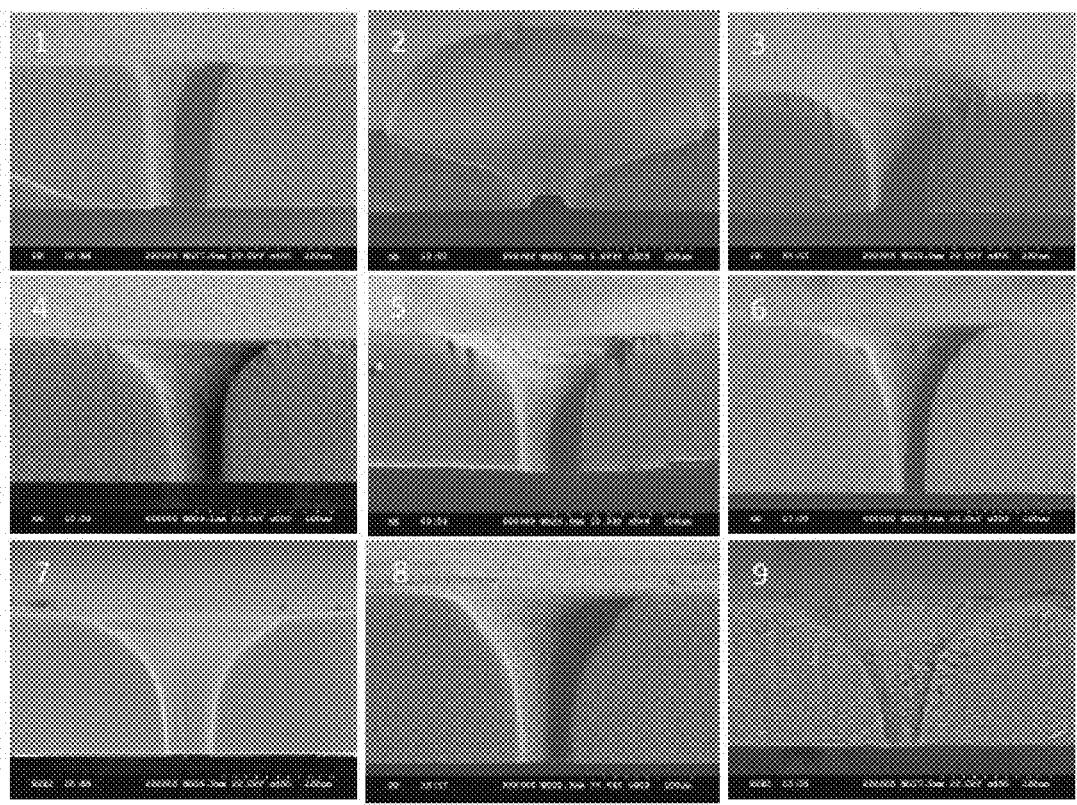
FIG. 9 illustrates cross sectional views of a micromachined, laser ablated generator plate structures according to implementations of the disclosure.
Figure 10:
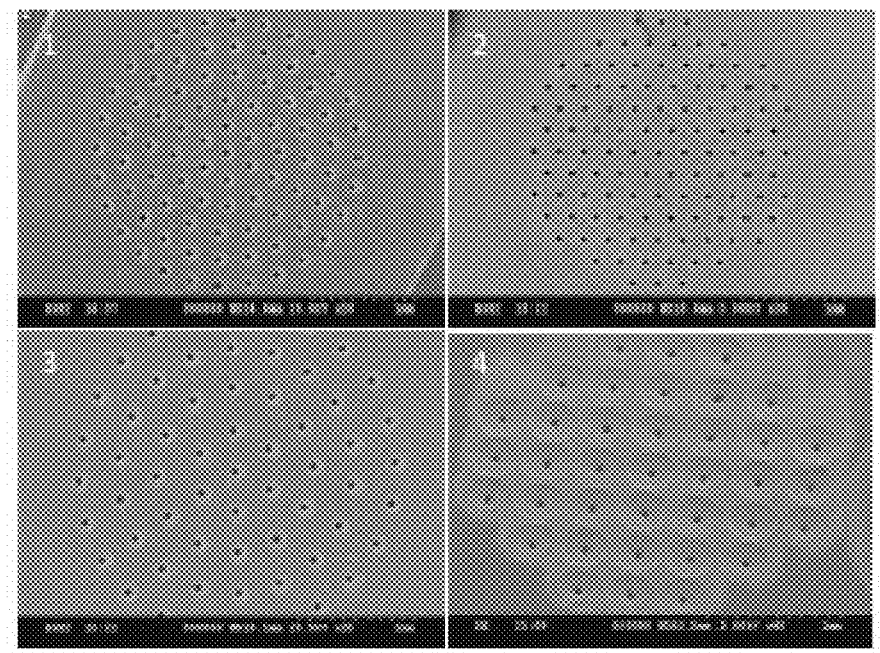
FIG. 10 illustrates spatial distribution of select opening geometries (shown in FIG. 9), according to implementations of the disclosure.
Figure 11:
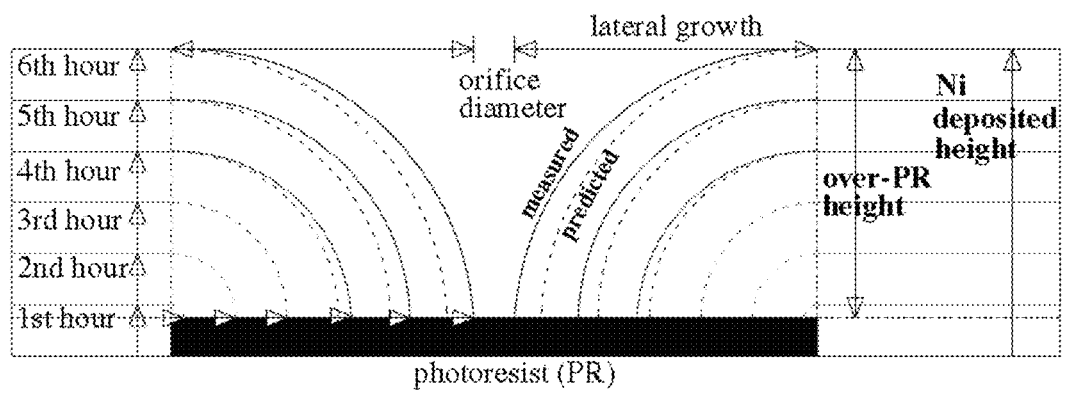
FIG. 11 illustrates a view of the opening forming process using UV LIGA, according to implementations of the disclosure.

FIG. 8 further shows exemplary generator plate structures which may serve as inputs for fabrication, e.g., via excimer laser ablation. Using excimer laser ablation as a tool for microfabricating generator plate nozzle structures, all of the design parameters described in FIG. 10 can be independently controlled and modified. FIG. 9 illustrates cross sectional views of a micromachined, laser ablated generator plate structures. All are micromachined from virgin PEEK with exception of (9) which is talc filled (20%). In addition, the spatial distribution of the nozzle array on the generator plate (membrane) can be controlled (FIG. 11). FIG. 10 illustrates spatial distribution of select opening geometries (shown in FIG. 9), shown as an array on the generator plate (membrane). These are viewed with the fluid entrance opening facing up.

The two-dimensional array displayed in FIGS. 9 and 10 provide an example of the flexibility that excimer laser ablation provides for microfabrication and surface structuring of polymers. Alternative processes for forming openings of a generator plate include the LIGA process. (E. W. Becker, et al., *Microelectron. Eng.* 4 (1986) 35-56), processes based on UV lithography, UV LIGA (H. Miyajima et al., *J. Microelectrochem. Syst.* 4 (1995) 220-229; C. H. Cheng, et al., *J. Microch. Microeng.* 15 (2005) 843-848). Reference to FIG. 11 provides a view of the opening-forming process using UV LIGA. Opening formation via UV LIGA employs an electroforming step in which the metal is deposited via electroforming onto the photoresist mold (C. H. Cheng, et al). The overdeposition results in the formation of a parabolic hole which is the opening.

In some implementations, the ejector plate 1602 and/or high modulus polymeric generator plate 1632 may be coated with a protective coating that is anti-contamination and/or anti-microbial. The protective coating can be conformal over all surfaces of the ejector plate and/or high modulus polymeric generator plate, including surfaces defining the openings 1626, portions of the openings (outer surface, inner surface, etc.). In other implementations, the protective coating can be applied over selected surfaces, e.g., the surfaces 1622, 1625, 1622*a*, 1625*a*, or surface regions, e.g., parts of such surfaces. The protective coating can be formed of a biocompatible metal, e.g., gold (Au), iridium (Ir), rhodium (Rh), platinum (Pt), palladium (Pd), titanium nitride (TN), chromium nitride (CrN), amorphous carbon, nickel-platinum alloy, nickel-palladium alloy, chromium carbon nitride, aluminum (Al), or alloys thereof, or a biocompatible polymer, polyamide imide, polyether ether ketone (PEEK), polypropylene (PP), or high density polyethylene (HDPE). Antimicrobial materials include metals such as silver, silver oxide, selenium or organic chlorides or organometallics such as alkylbenzyldimethylammonium (benzalkonium) chloride, or transition metal complexes of 1,1'-diacetylferrocene-derived thiocarbohydrazone, for example, or polymers such as carboxyl-containing ethylenecopolymers such as poly(ethylene-co-acrylic acid) (E/AA), and 8-hydroxyquinolinium ionomers. The protective coating can be in direct contact with the fluid 1610 or the droplets 1612. The coating may provide an inert barrier around the fluid or may inhibit microbial growth and sanitize the fluid 1610 and/or the droplets 1612.

Additionally, surface 1622 or 1622*a* of ejector plate 1602 or high modulus polymeric generator plate 1632 may be coated with a hydrophilic or hydrophobic coating. Additionally, the coating may be coated with a protective layer. The surface may also be coated with a reflective layer. A coating layer may be both protective and reflective. Alternatively, the surface may have been formed to be reflective. For example, the surface may be made of stainless, nickel-cobalt, or other reflective material. A surface may have been formed or polished to be reflective. In addition to making the surface reflective, the surface may also be backlit on its surface or around its perimeter. In ophthalmic applications, a reflective surface aids the user in aligning the ejector assembly with the eye.

If desired, surfaces of the ejector assembly may include coatings that may be pre-formed by dipping, plating, including electroplating, or otherwise encapsulating, such as by molding or casting. The coatings may also be deposited by suitable deposition techniques such as sputtering, vapor deposition, including physical vapor deposition (PAD) and chemical vapor deposition (COD), or electrostatic powder deposition. The protective coating may have a thickness of about less than 0.1 μm to about 500 μm. It is desirable that the coating adhere to the plate sufficiently to prevent delamination when vibrating at a high frequency.

Piezoelectric actuator 1604 may be formed from any suitable material known in the art. By way of example, in some implementations, the piezoelectric actuator can be formed from lead zirconate titanate (Pb[Zr(x)Ti(1−x)]O3) (PZT), barium titanate (BaTiO3), bariumzirconate titanate (Ba(Zr,Ti)O3), BiFeO3-based ceramic, bismuth sodium titanate (BNT) material or a bismuth potassium titanate (BKT) material or polymer-based piezoelectric materials, such as polyvinylidine fluoride. The electrodes 1606*a* and 1606*b* can be formed of suitable conductors including gold, platinum, or silver. Suitable materials for use as the adhesive 1628 can include, but not be limited to, adhesives such as loctite E-30CL or Loctite 480 or 380 epoxies or other suitable super glue such as Loctite ultra gel, epoxies, silver-epoxy or nickel-epoxy paste. One example of a conductive adhesive includes an epoxy paste formulated using Ni powder and Loctite E-30CL. The reservoir 1620 may be formed of a polymer material, a few examples of which include Nexcel Latitude ML29xxC, Rollprint-ClearFoil V, low density and high density polyethylene (LDPE, HDPE), or ethylene vinyl acetate/polyvinylidene chloride (EVA/PVDC) coextruded films.

In certain aspects of the disclosure, the ejector mechanism may be configured so as to facilitate actuation of the ejector plate, and thereby the high modulus polymeric generator plate, by the piezoelectric actuator. As described above, the high modulus polymeric generator plate may be configured to optimize ejection of a fluid of interest. For example, the aspect ratio of the openings of the high modulus polymeric generator plate may be selected based, in part, on fluid properties, such that the general thickness of the high modulus polymeric generator plate ranges from about 50 μm to about 500 μm, as described above.

Without being limited by theory, in certain implementations, actuation of the ejector mechanism may be optimized using configurations including a high modulus polymeric generator plate coupled to an ejector plate, as described herein. In addition, reducing the surface area of the high modulus polymeric generator plate (i.e., the central region having one or more openings) likewise reduces manufacturing costs, reduces potential related manufacturing defects, and increases manufacturing efficiencies and output. In certain aspects, the ejector plate may be sized and shaped in a manner to facilitate actuation of the ejector mechanism (i.e., actuation of the ejector plate and thereby the high modulus polymeric generator plate). By way of example, configurations of the ejector plate may effectuate actuation of the ejector mechanism through selection of properties (e.g., size, shape, material, etc.) that facilitate flex of the ejector plate, and thereby vibration of the high modulus polymeric generator plate. For instance, the ejector plate may have a thickness generally ranging from about 10 μm to about 400 μm, from about 20 μm to about 100 μm, from about 20 μm to about 50 μm, about 30 μm to about 50 μm, etc. Again, without being limited by theory, in certain implementations, direct actuation of a relatively thinner ejector plate (compared to the high modulus polymeric generator plate), may be more optimal.

In accordance with certain implementations of the disclosure, the configuration of the ejector plate and the high modulus polymeric generator plate may be selected such that the center region of the high modulus polymeric generator plate including openings (e.g., the "active region" of the high modulus polymeric generator plate) produces a symmetric oscillation with a normal mode of oscillation. Without being limited by theory, in certain implementations, configurations of the ejector plate and high modulus polymeric generator plate may be selected such that 0.2 normal mode and 0.3 normal mode of oscillation of the active region of the high modulus polymeric generator plate is observed. The mode is associated with a maximum amplitude and displacement of the active region, wherein the mode is designated as (d,c) where d is the number of nodal diameters and c is the number of nodal circles.

The magnitude and frequency of the ejector plate vibration can also be controlled by controlling the voltage pulses applied to the electrodes 1606a, 1606b, e.g., a voltage differential of 40 or 60 V may be applied to the electrodes. As discussed above, the pulses are created by voltage differentials that deflect ejector plate 1602, and thereby high modulus polymeric generator plate 1632. In some implementations, one of the electrodes 1606a or 1606b is grounded and voltage pulses, e.g., bipolar pulses, are applied to the other one of the electrodes 1606a or 1606b e.g., to vibrate the ejector plate 1602. By way of example, in one implementation, the piezoelectric actuator 1604 can have a resonant frequency of about 5 kHz to about 1 MHz, about 10 kHz to about 160 kHz, about 50-120 kHz to about 50-140 kHz, etc., e.g., 108-130 kHz. The applied voltage pulses can have a frequency lower, higher, or the same as the resonant frequency of the piezoelectric actuator 1604.

In certain implementations, delivery time of the droplets is about 0.1 ms to about several seconds. Without wishing to be bound by theory, it is believed that human eyes take about 300 ms to about 400 ms between blinks. Therefore, for implementations where delivery is desired to be between blinks, the delivery time may be about 50 ms to about 300 ms and more particularly 25 ms to 200 ms. In one implementation, the delivery time is 50 ms to 100 ms. In this way, the ejected droplets can be effectively delivered and deposited in the eye during a blinking cycle of the eye. In some implementations, for example over-the-counter saline dispensers, the delivery time can be as long as several seconds, e.g., 3-4 seconds, spanning several blink cycles. Alternatively, a single delivery can be administered by several bursts or pulses of droplet ejection. Additionally, and not intending to be limited by theory, pulsing may be used to reduce the peak amplitude of the droplet airstream by spreading the impulse out over time. Therefore, the pressure of the ejection on the target may be mitigated. Furthermore, pulsing may also reduce droplet agglomeration and result in less entrained air generation. By way of example, pulses of 25 ms can be administered with stop times of 25 ms separating the pulses. In one implementation, the pulses may be repeated for a total of 150 ms total time.

The ejector assembly described herein may be incorporated into an ejector device and system. Exemplary ejector devices and systems are illustrated in U.S. application Ser. No. 13/184,484, filed Jul. 15, 2011 and U.S. Application No. 61/569,739, filed Dec. 12, 2011, the contents of which are herein incorporated by reference for the purpose of such disclosures.

Many implementations of the invention have been disclosed. This disclosure contemplates combining any of the features of one implementation with the features of one or more of the other implementations. For example, any of the ejector mechanisms or reservoirs can be used in combination with any of the disclosed housings or housing features, e.g., covers, supports, rests, lights, seals and gaskets, fill mechanisms, or alignment mechanisms. Further variations on any of the elements of any of the inventions within the scope of ordinary skill is contemplated by this disclosure. Such variations include selection of materials, coatings, or methods of manufacturing. Any of the electrical and electronic technology can be used with any of the implementations without limitation. Furthermore, any networking, remote access, subject monitoring, e-health, data storage, data mining, or internet functionality is applicable to any and all of the implementations and can be practiced therewith. Further still, additional diagnostic functions, such as performance of tests or measurements of physiological parameters may be incorporated into the functionality of any of the implementations. Performance of glaucoma or other ocular tests can be performed by the devices as a part of their diagnostic functionality. Other methods of fabrication known in the art and not explicitly listed here can be used to fabricate, test, repair, or maintain the device. Furthermore, the device may include more sophisticated imaging or alignment mechanisms. For example, the device or base may be equipped with or coupled to an iris or retina scanner to create a unique identification to match a device to the user, and to delineate between eyes. Alternatively, the device or base may be coupled to or include sophisticated imaging devices for any suitable type of photography or radiology.

To assist in understanding the present invention, the following Example is included. The experiments described herein should not, of course, be construed as specifically limiting the invention and such variations of the invention, now known or later developed, which would be within the purview of one skilled in the art are considered to fall within the scope of the invention as described herein and hereinafter claimed.

EXAMPLES

Example A: Modes of Operation

Figure 5:
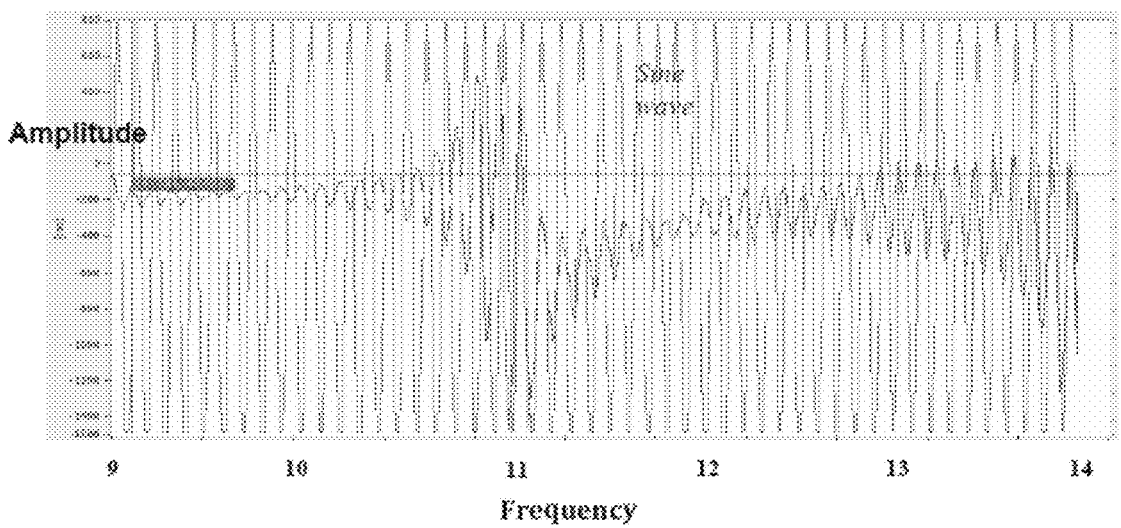
FIG. 5 illustrates a frequency scan of an ejection assembly vs. oscillation amplitude, according to an implementation of the disclosure.

Although many arrangements are possible, one implementation uses a piezoelectric-driven ejector mechanism which includes a 6 mm outer diameter, 300 μm thick PEEK generator plate that is bonded to a 20 mm outer diameter, 50 μm thick 304 stainless steel ejector plate annulus. The ejector plate annulus includes a 4 mm diameter central opening which is aligned with the PEEK generator plate, and a 16 mm outer diameter, 8 mm inner diameter piezoelectric actuator is attached directly to the ejector plate. A modulation frequency of approximately 108 kHz to over 140 kHz is applied to the piezoelectric actuator, causing the ejector plate to oscillate. Digital holographic microscopy images are captured to observe oscillation of the high modulus polymeric generator plate. By way of example, with reference to FIG. 5, a frequency scan of the implemented ejection assembly vs. oscillation amplitude was performed to provide for identification of optimal resonant frequency and range of frequencies at which the maximum out of plane displacement of the generator plate is achieved. Out of plane oscillation amplitude of the generator plate as a function of drive frequency and excitation with a sine wave at 60 Vpp is illustrated in FIG. 5, with an onset of maximum amplitude of oscillation at ~108 kHz, and a maximum amplitude of ~2.3 microns at 110 kHz. Overlaid onto the amplitude profile in FIG. 5 is the sine wave of the 60 Vpp used to drive the piezoelectric actuator.

Figure 3:
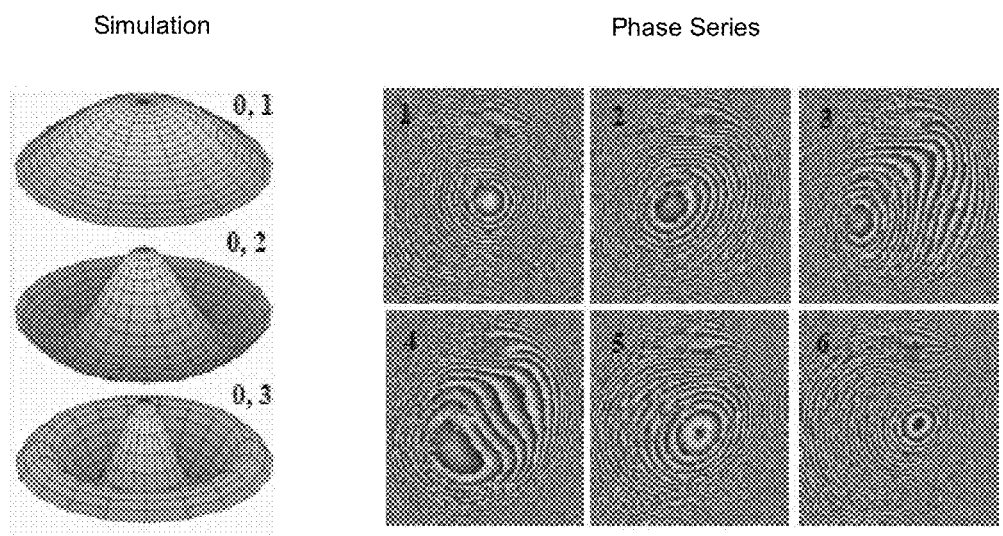
FIG. 3 illustrates modes of operation of an active region of an implementation of a high modulus polymeric generator plate, and digital holographic microscopy image of oscillation of the high modulus polymeric generator plate according to an implementation of the disclosure.
Figure 4A:
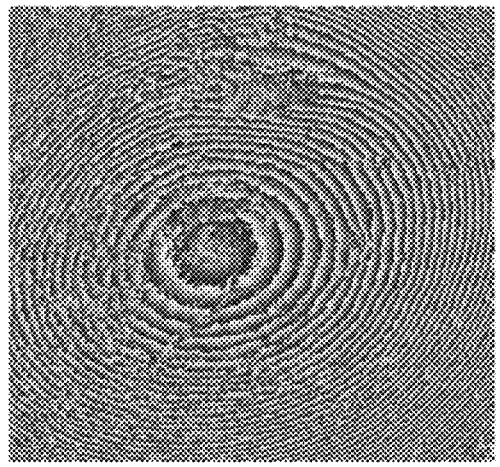
FIGS. 4A-4B illustrate an active region of an implementation of a high modulus polymeric generator plate, and a digital holographic microscopy image of oscillation of the high modulus polymeric generator plate according to an implementation of the disclosure.
Figure 4B:
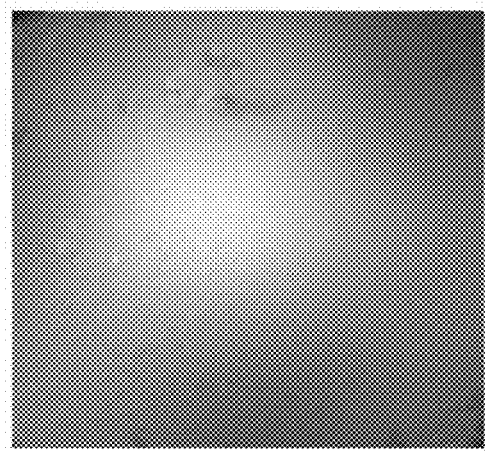

The piezoelectric-actuated PEEK membrane displays a periodic oscillation which spans a frequency range from about 108 kHz to over 140 kHz and a maximum oscillation amplitude of ~2 microns at 110 kHz. Dynamic imaging of oscillation modes confirms the normal modes of oscillation as 0.1 and 0.2 in the active ejector region of the PEEK membrane. FIG. 3 illustrates Digital Holographic Microscopy of an ejector assembly comprising a generator plate formed from PEEK operating at a modulation frequency=110 kHz. Phase series display periodic oscillations of the PEEK generator plate at resonance (1-6). With reference to FIG. 4A (Phase) and FIG. 4B (Topograph), Digital Holographic Microscopy, phase and amplitude images display the topography at resonance (110 kHz) and resultant symmetric oscillation of the PEEK membrane are illustrated. Computer simulation confirms experimental observation of the normal modes of oscillation 0.1 and 0.2 in bonded PEEK membrane. This mode is associated with a maximum amplitude and a measured displacement of ~2 μm at the center, active region of the generator plate.

Example B: Spray Performance

Ejector assembly performance may be evaluated over a range of fluid viscosities from low viscosity, e.g., using distilled water (viscosity 1.017 cP), to high viscosity, e.g., using medications such as an ophthalmic emulsion of cyclosporine such as Restasis™ (dynamic viscosity=18.08 cP). By way of example, ejector assembly performance may be evaluated by analyzing fluid mass ejection as a function of actuation frequency.

Figure 6:
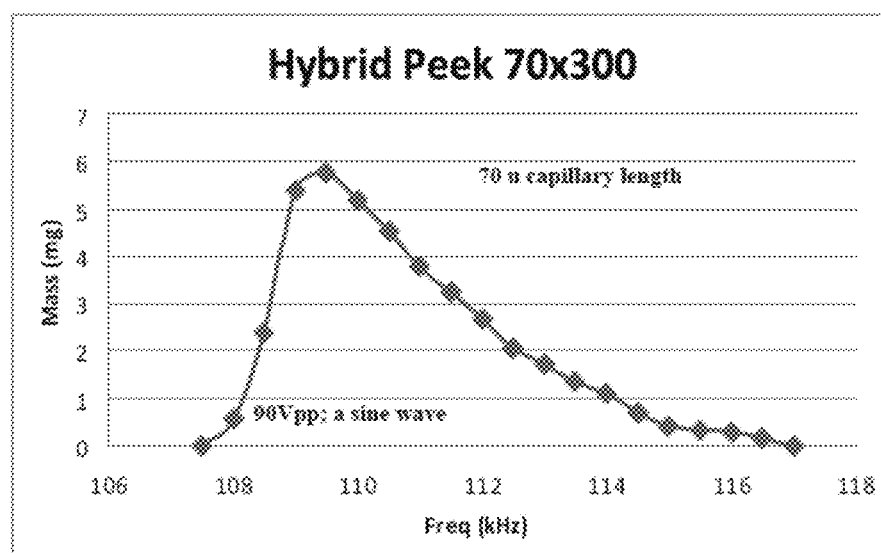
FIG. 6 illustrates mass ejection vs. frequency for water using an ejector assembly according to an implementation of the disclosure.

The mass ejection profile closely tracks the membrane oscillation amplitude with a maximum mass ejection at ~110 kHz and maximum oscillation amplitude of ~2 microns at 110 kHz. Ejection of low viscosity fluids (water) was observed with capillary lengths of both 70 and 120 microns. With reference to FIG. 6, mass ejection vs. frequency for water using a 300 μm thick PEEK generator plate with 70 μm capillary channel length is illustrated, with an onset of maximum amplitude at 108 kHz and a maximum amplitude of 2.3 μm at 110 kHz, which coincides with a maximum water ejection mass (average over 5 ejections).

Example C: Effect of Capillary Length

Figure 7A:
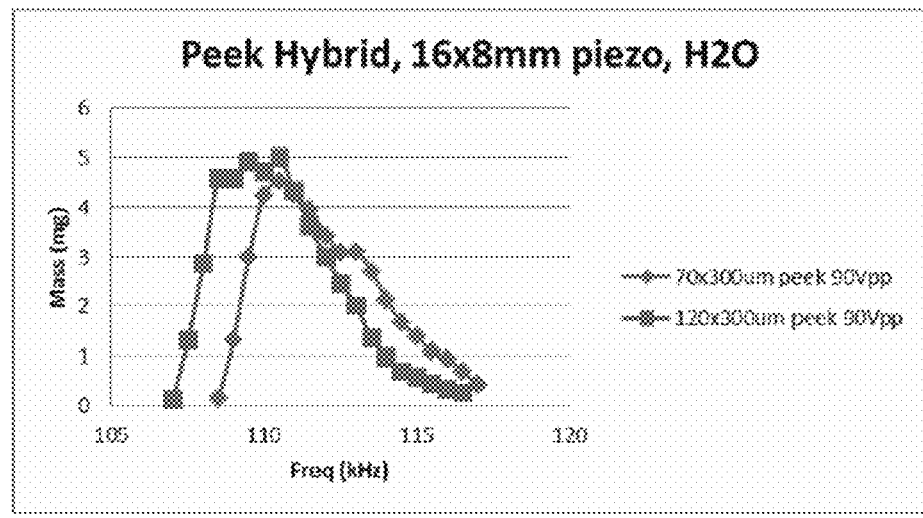
FIGS. 7A-7B illustrate mass ejection vs. frequency for water and Restasis™ using an ejector assembly according to an implementation of the disclosure.
Figure 7B:
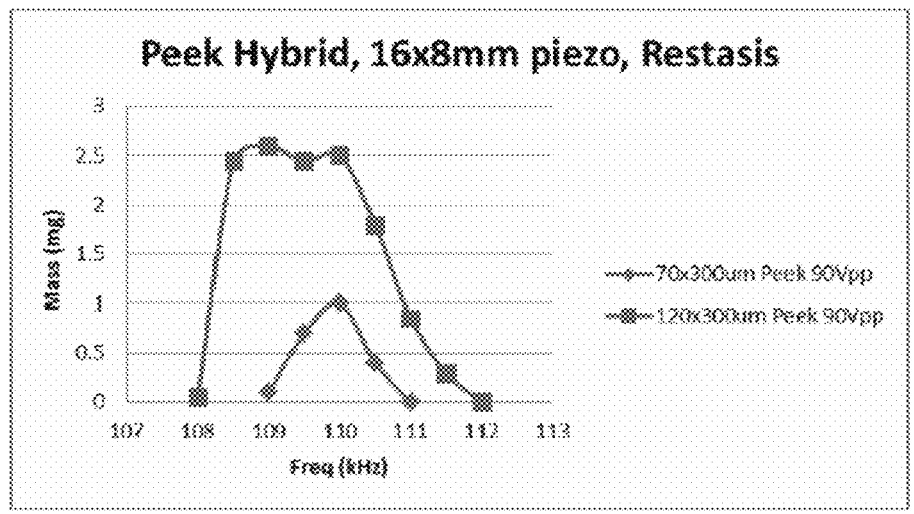

In certain implementations of ejector mechanisms of the disclosure, capillary length of the openings of the generator plate may affect spray performance. As illustrated in FIGS. 7A-7B, mass ejection vs. frequency reveals a shift in frequency, to lower frequencies, for water ejected from PEEK membranes having 120 micron long capillary channels. However, for high viscosity fluids such as Restasis™ (dynamic viscosity=18.08 cP), a significant increase in the mass ejection peak (2.5×) for PEEK membranes with 120 micron long capillary channels vs. membranes with 70 micron long capillary channels is observed.

More particularly, FIG. 7A illustrates ejection of Newtonian fluids (water), while FIG. 7B illustrates ejection of Non-Newtonian fluids (Restasis). FIG. 7A shows that an increase in capillary length leads to an increase in resistance and load on the fluid as it exits the opening. This mass loading effect leads to a shift in the peak ejection frequencies. FIG. 7B shows that mass ejection through a capillary is affected by capillary length.

As shown, the increase in capillary length from 70 microns to 120 microns and associated change in entrance cavity contour leads to about a 2.5 fold increase in ejected mass. The increase in fluid acceleration along the capillary (e.g., as shown in FIG. 15), coupled with the 7.5 fold reduction in diameter from the entrance cavity to the exit orifice, leads to an increased pressure gradient and subsequent increase in shear force. The result is a decrease in viscosity of the fluid and an increase in ejected volume.

Example D: Effect of Eigenmode

Figure 13:
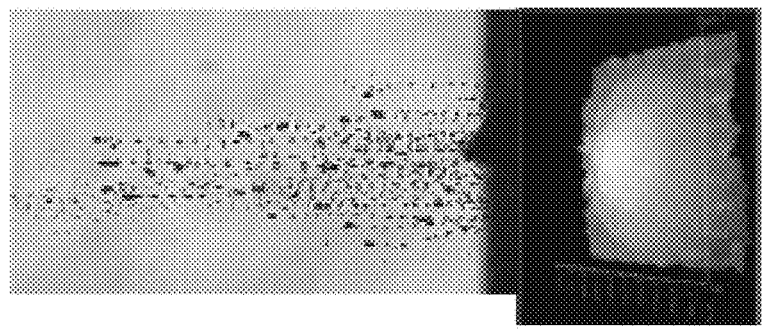
FIG. 13 illustrates a high speed image of a droplet spray overlaid with a digital holographic image of a normal mode of operation of exemplary ejector mechanisms of the disclosure.

In certain implementations of ejector mechanisms of the disclosure, the eigenmode of the generator plate may affect the shape of the generator plate, and the resulting spray, during excitation. FIG. 13 shows a high speed image frame representative of an ejected spray from a ejector mechanism of the disclosure overlaid with digital holographic image captured from a similar ejector mechanism, which displays the normal mode of generator plate oscillation at 140 kHz.

Example E: Simulation of Pressure Driven Flows

Forces acting on fluids include, pressure gradient, friction forces and volume forces. The magnitude and time during which such forces act on a fluid may be controlled by, e.g., changing the fluid entrance diameter, fluid exit diameter, capillary length, and material properties (mechanical, chemical and surface topography). By way of example, flow simulation through an opening of a generator plate may be modeled based on, e.g., the opening designs of FIGS. 14A-14B (100 μm thick PEEK; 40 micron diameter exit orifice and 240 micron diameter entrance orifice), using PEEK material properties and fluid viscosities of 1 Pa-s, and 18 Pa-s (to simulate viscosities of water and Restasis, respectively).

FIG. 15 shows a simulation of a pressure driven flow through in a capillary. The flow simulation was solved assuming an oscillating pressure from 0 to 2000 Pa and an oscillating frequency of 120 kHz. The simulation includes both low viscosity (1 mPa-s), Newtonian (FIG. 15A) and high viscosity (18 mPa-s), non-Newtonian fluids (FIG. 15B).

In the simulation of low viscosity (1 mPa-s), Newtonian (water) (FIG. 15A) and high viscosity (18 mPa-s), non-Newtonian fluids (Restasis) (FIG. 15BB), the maximum velocity is located at the nozzle ejector exit region where the orifice is at its minimum cross section. The fluid velocity, while inside the exit orifice before emerging as a spray is from 60 to 65 meters/sec (m/s). The computed velocity for water as it emerges from the nozzle orifice has a velocity from 5 to 10 m/s, while the exit velocity for Restasis is from 5 to 20 m/s.

Figure 16A:
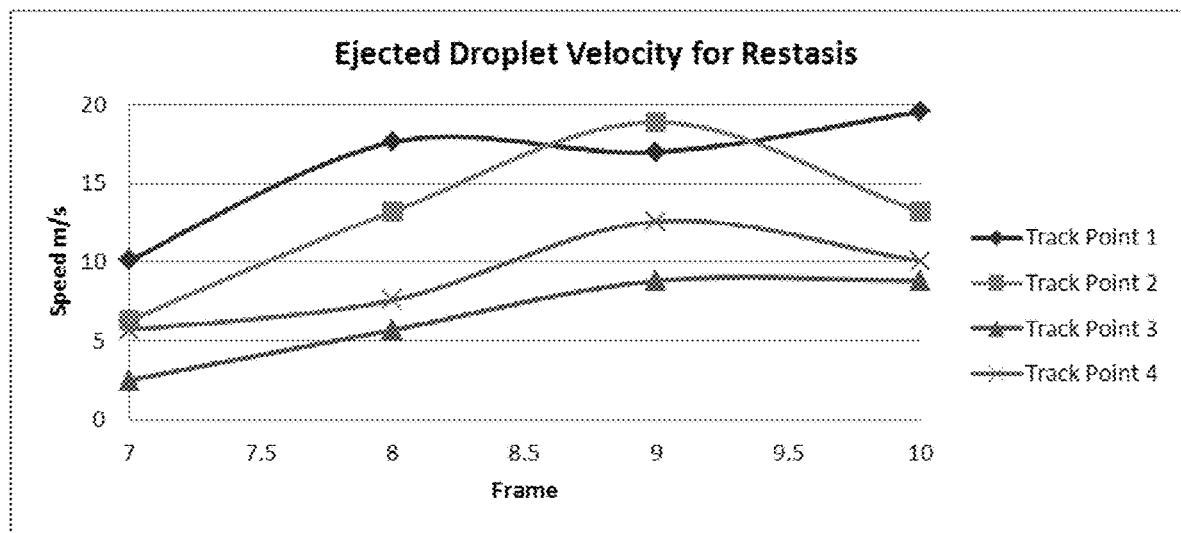
FIGS. 16A-16B illustrate ejected droplet velocity over time, according to implementations of the disclosure.
Figure 16B:
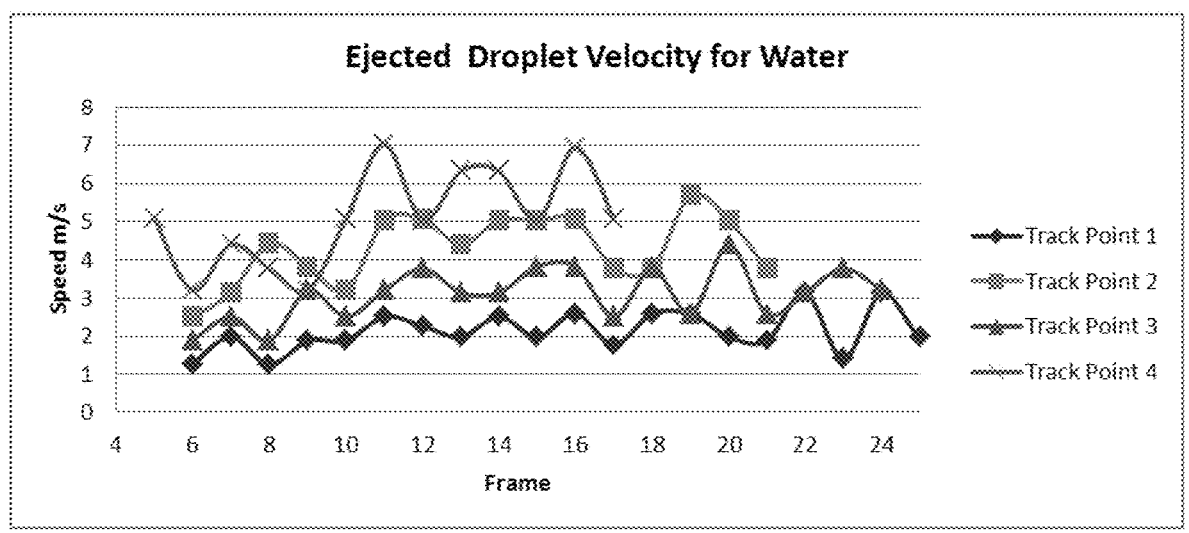

These simulated ejected velocities compare favorably with measured velocities for water and Restasis ejected from a NiCo ejector. With reference to FIGS. 16A-16B, high speed videography (not shown) was used to capture and measure single droplet speed as it emerged from the opening. (20 mm, OD NiCo membrane with 40 micron exit holes and 160 micron thick, and actuated with a 16 mm, OD and 8 mm, ID piezoelectric element (PZT) at an excitation voltage of 90 Vpp and at a frequency of 132 kHz). These data show the ejected speed for water as from 1 to 7 m/s (FIG. 16B), while Restasis emerged from the nozzle at speeds from 5 to 20 m/s (FIG. 16A).

Example F: Shear Rate Dependence Viscosity

The purpose of the testing was to determine if the viscosity of the Restasis® was shear independent (Newtonian) or shear dependent (non-Newtonian). For Newtonian fluids, the pressure drop increases linearly with flow rate and the measured viscosity does not depend upon applied deformation rate or stress. Non-Newtonian fluids or complex fluids, however, can display shear thinning or shear thickening, and the pressure drop versus flow rate data must be analyzed using Weissenberg-Rabinowitch-Mooney equation.

The shear rate dependence of Restasis was measured by rheometery. This method is commonly used to measure the way a liquid, suspension or slurry flows in response to applied forces. An MCR 302 rheometer by Anton Paar was used to characterize the flow properties of three 0.4 ml vials of Restasis® lot 74381. The rheometer configuration utilized was as follows: MCR 302 rheometer; P-PTD200/80 Peltier controlled lower plate chamber; and CP50-0.5 measuring cone (50 mm diameter; 0.5° cone angle, 0.504 cone truncation (measuring gap), 0.29 ml fill volume. The testing was conducted 23±0.1° C. Within the time scale of one single flow curve, the samples were not volatile and did not appear to sediment therefore no precautions were necessary with respect to evaporation control or mixing.

For sample loading, the vial cap was removed in the full 0.4 ml dose was squeezed onto the rheometer's lower plate. A sharp point was used to pop any entrapped air bubbles visible in the sample. Entrapped air in a sample will impact accuracy and reproducibility in viscosity measurements. While the fill volume for the measuring cone used was 0.29 ml, the full 0.4 ml dose was used. Attempting to trim the excess sample would possibly introduce error and disturb structure within the sample around the edge of the cone.

A thirty second hold after sample loading and attainment of the measuring gap was used to a) ensure the sample temperature was at equilibrium at 23° C. and b) ensure that any structural damage occurring during loading was allowed to recover. A flow curve is a steady shear (rotational) test is conducted by ramping the shear rate and measuring shear stress required to obtain the applied shear rates in the given sample. From this, viscosity is determined as the ratio of shear stress to shear rate.

Flow curve results may be plotted as Viscosity versus Shear Rate which is called a viscosity curve. They may also be plotted as Shear Stress versus Shear Rate which is called simply a flow curve. Generated flow curves present viscosity in mPa·s. Shear rate is expressed in 1/s ($s^{-1}$ or reciprocal second) and shear stress is expressed in Pa (pascal). Instrument calibration was verified prior to testing using traceable viscosity standard Cannon S200 (results not shown)

Figure 17:
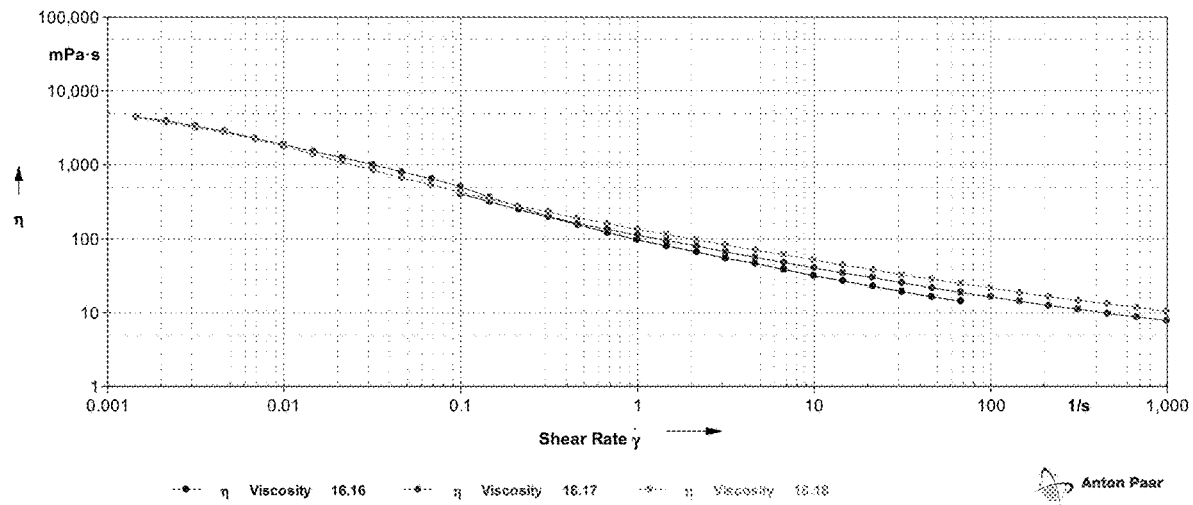
FIG. 17 illustrates a replicate analysis demonstrating the shear thinning behavior of Restasis.
Figure 18:
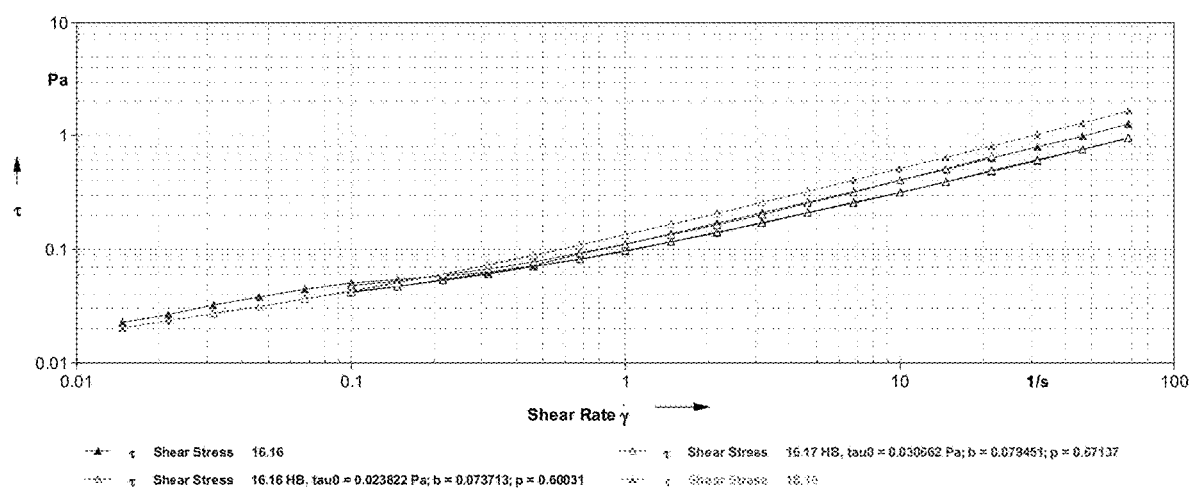
FIG. 18 illustrates the same flow curve data as in FIG. 17, but plotted as shear stress versus shear rate.

FIG. 17 shows a replicate analysis of three samples demonstrate the shear thinning behavior of Restasis, i.e. as shear rate is increased the sample viscosity decreases. The drop in measured viscosity for each sample is dramatic. Slight variation in the measured viscosity is most likely a result of the presence of entrapped air bubbles in the Restasis emulsion which could not be removed and/or the inability to dose out precisely the same volume for each sample loading. FIG. 18 displays the same flow curve data as in FIG. 17, but plotted as shear stress versus shear rate. The samples did exhibit a weak yield point at shear rates of ~0.15 1/s and corresponding stress of 0.05 Pa, which is expected in an emulsion. A yield stress means that a certain amount of applied stress must occur in order to overcome the internal structure in the samples so that flow may begin.

The flow curves indicate that this material exhibits complex, shear thinning behavior. Describing this sample by a single viscosity value requires identification of the shear rate at that point. In the case of non-Newtonian materials, viscosity is not a material function thus the conditions under which the viscosity was measured must be stated. It was found that Restasis has a viscosity, at 23° C., of 111 mPa·s at 1 1/s while having a viscosity if 8 mPa·s at 1,000 1/s.

Example G: Effect of Capillary Channel Geometry and Placement

Figure 19A:
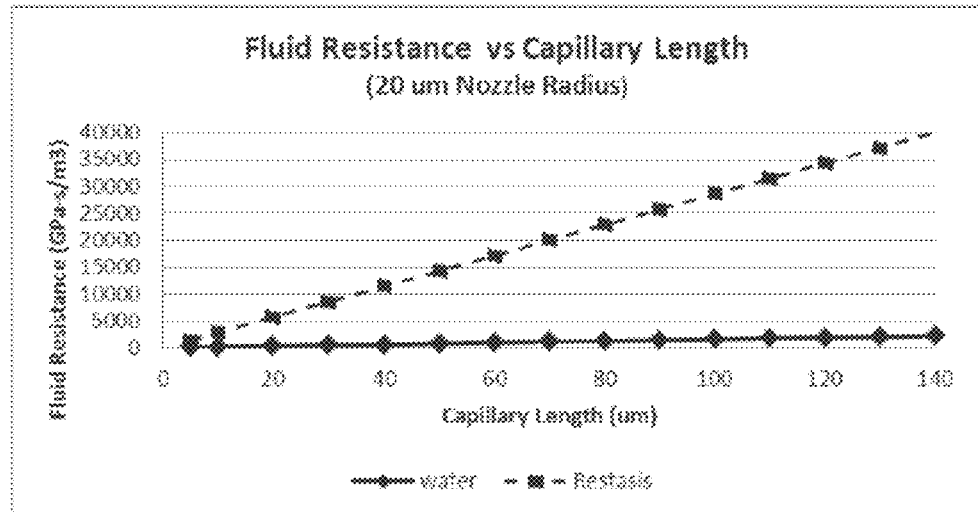
FIGS. 19A-19C illustrate fluid resistance as a function of capillary length, according to implementations of the disclosure.
Figure 19B:
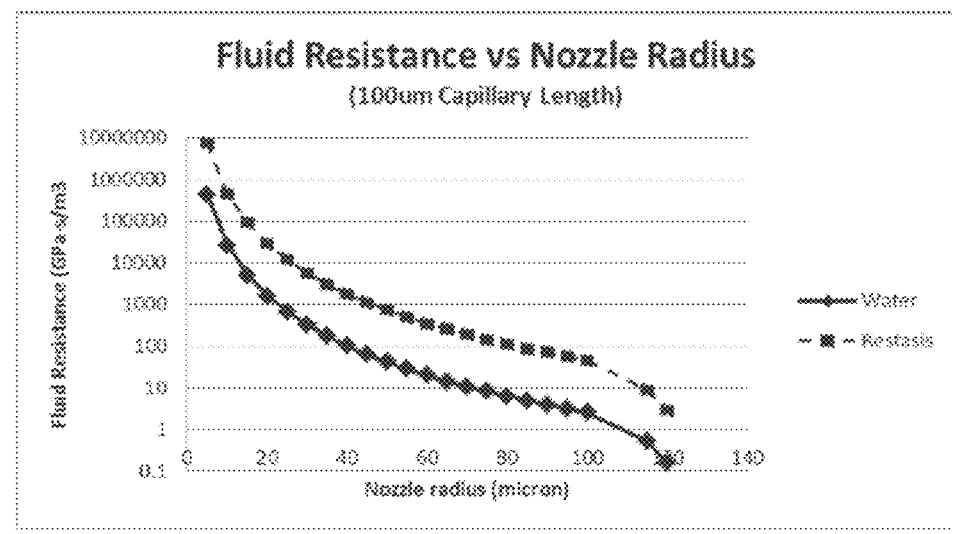
Figure 19C:
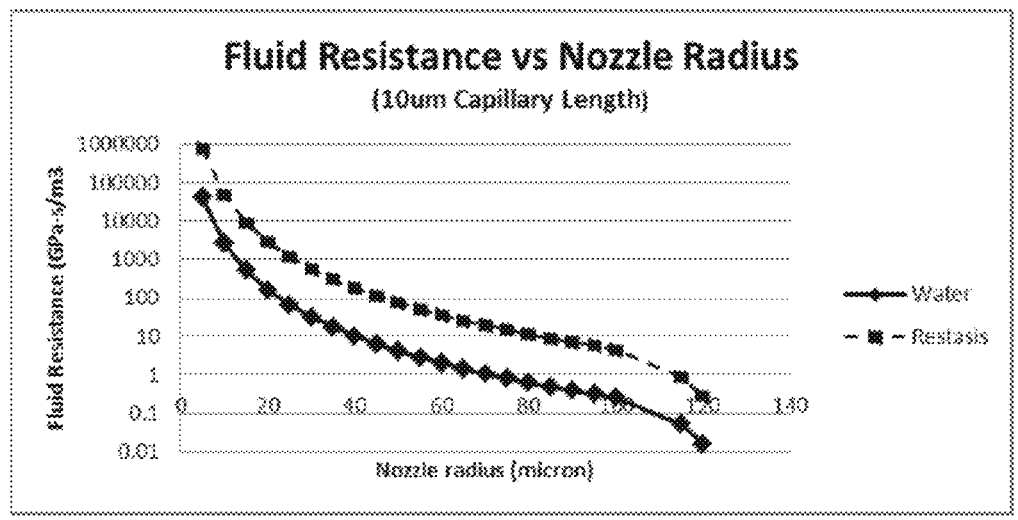
Figure 21A:
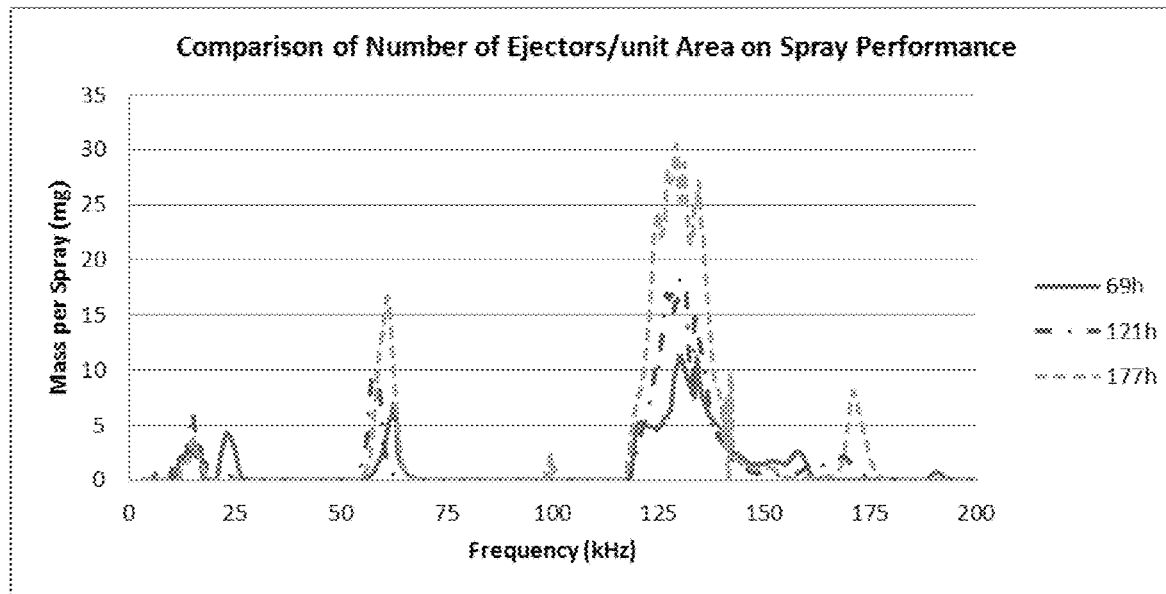
FIGS. 21A-21B illustrate spray performance as a function of the number of openings on a generator plate, according to implementations of the disclosure.
Figure 21B:
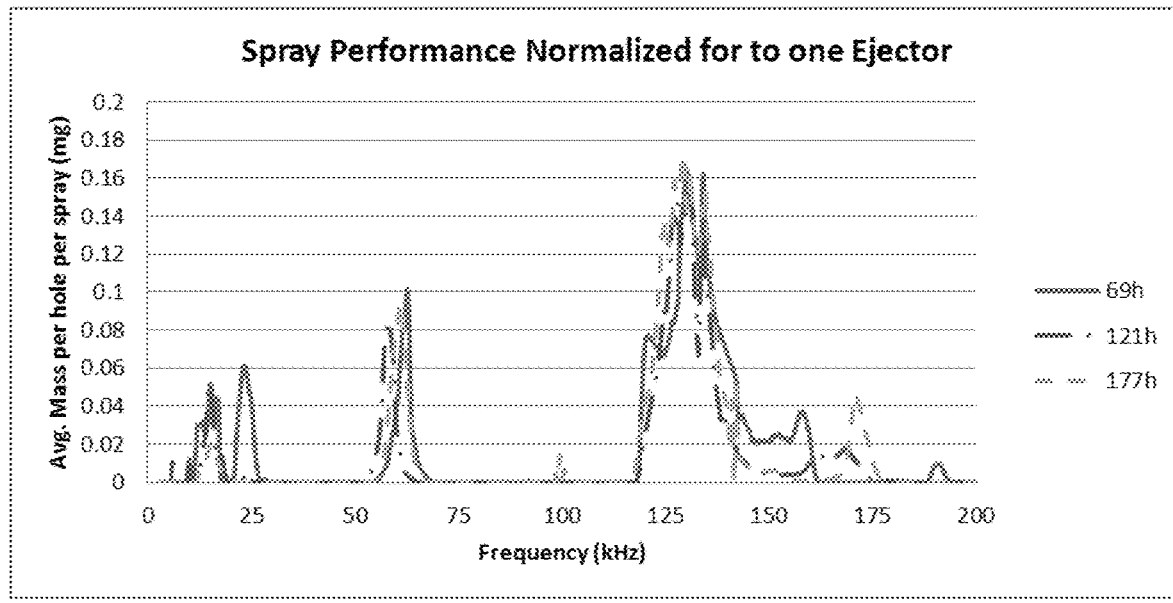
Figure 22A:
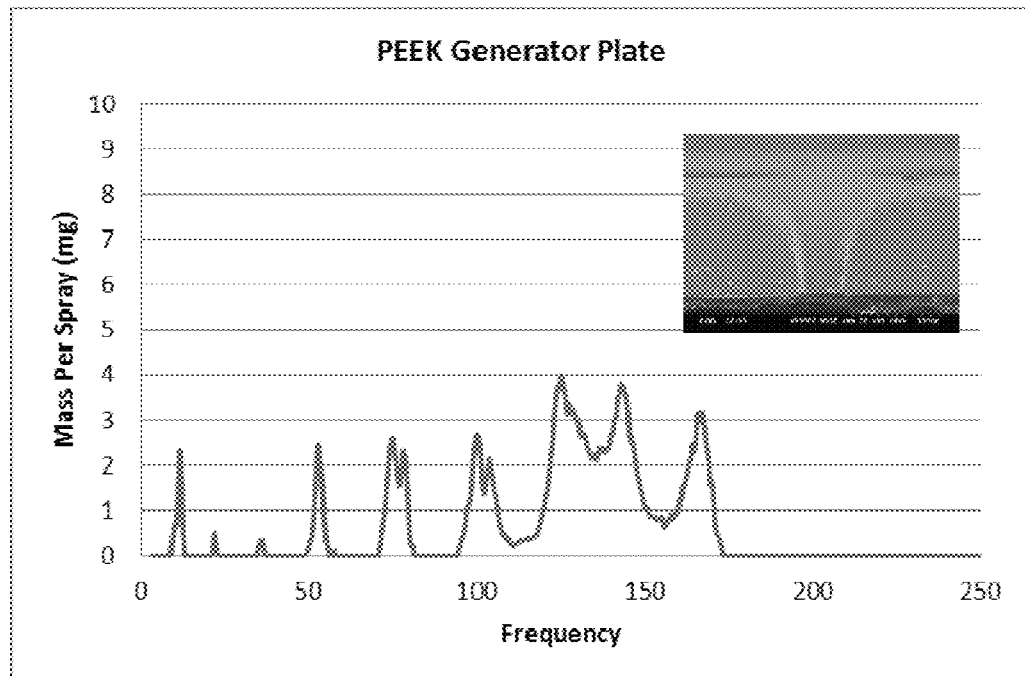
FIGS. 22A-22B illustrate spray performance as a function of the polymer modulus of a generator plate, according to implementations of the disclosure.
Figure 22B:
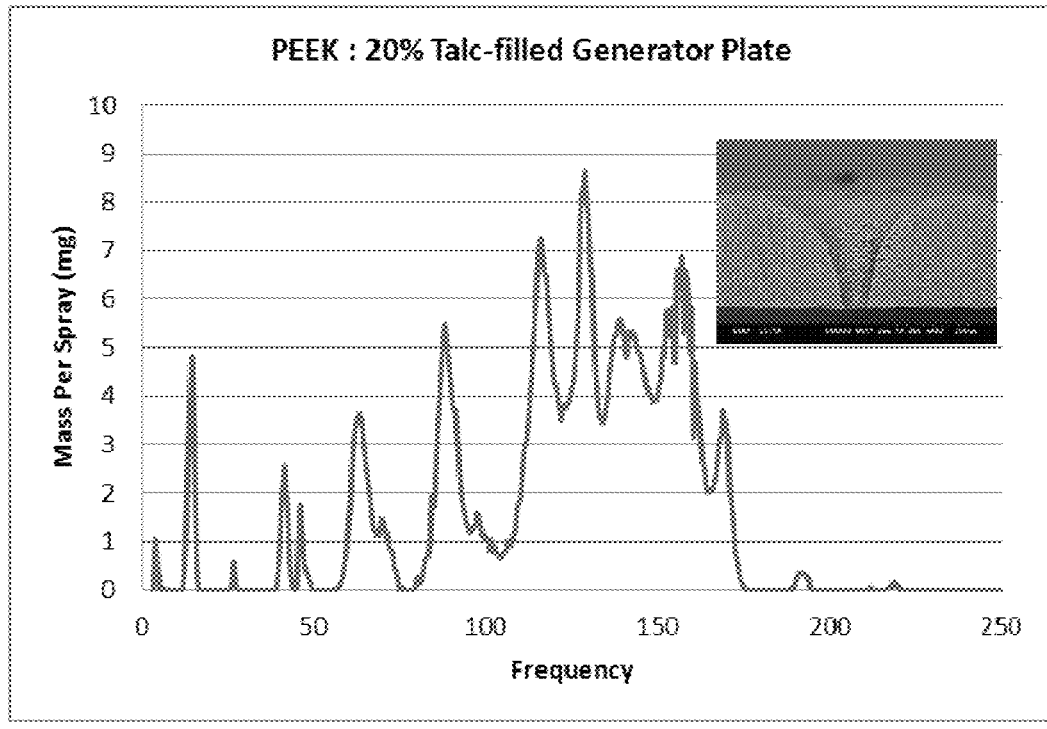

In certain implementations of ejector mechanisms of the disclosure, capillary channel geometry and placement may affect spray performance. FIGS. 19A-19C show that fluid resistance displays a linear relationship as a function of capillary length.

The hydraulic resistance for straight channels with different cross sectional shapes is shown below. The numerical values are calculated using the following parameters: =1 mPa s (water), L=1 mm, a=100 um, b=33 um, h=100 um, and w=300 um.

| shape | | $R_{hyd}$ expression | $\dfrac{R_{hyd}}{[10^{11} \frac{\text{P a s}}{\text{m}^3}]}$ | reference |
|---|---|---|---|---|
| circle |  | $\dfrac{8}{\pi} \eta L \dfrac{1}{a^4}$ | 0.25 | Eq. (2.30b) |
| ellipse | 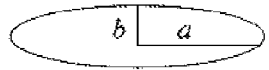 | $\dfrac{4}{\pi} \eta L \dfrac{1+(b/a)^2}{(b/a)^3} \dfrac{1}{a^4}$ | 3.93 | Eq. (2.29) |
| triangle |  | $\dfrac{320}{\sqrt{3}} \eta L \dfrac{1}{a^4}$ | 18.48 | Eq. (2.37) |
| two plates | 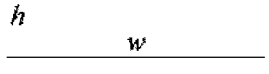 | $12\eta L \dfrac{1}{h^3 w}$ | 0.40 | Eq. (2.53) |
| rectangle |  | $\dfrac{12\eta L}{1 - 0.63(h/w)} \dfrac{1}{h^3 w}$ | 0.51 | Eq. (2.49) |
| square | 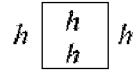 | $\dfrac{12\eta L}{1 - 0.917 \times 0.63} \dfrac{1}{h^4}$ | 2.84 | Exercise 3.4 |

With reference to FIGS. 20A-20B, (6 mm, OD, 100 u thick PEEK membrane 20 mm, mounted on a 20 mm, OD. and 4 mm, ID, 50 u thick stainless steel (304 or 316L) annulus and actuated by a 14 mm, OD and 13 mm, ID piezoelectric element (PZT)), placement of openings in the generator plate has a effect on spray performance. As shown in FIG. 20A, circular symmetric placement of openings leads to about a 2-3 fold increase in spray volume (mass deposition), as compared to a square opening array (FIG. 20B).

FIG. 21A-21B shows spray performance is also increased by increasing the number of openings in a generator plate. The effect of increased number of ejector holes per unit area of the active area is demonstrated in FIG. 21A, with a 3 fold increase in ejected mass at ~130 kHz when the number of holes are increased from 69 to 177 holes. FIG. 21B illustrates normalization of ejected volume (mass) per unit number of holes, showing the number of holes as the multiplicative factor.

Example H: Effect of Polymer Modulus

In certain implementations of ejector mechanisms of the disclosure, polymer modulus may affect spray performance. FIG. 22A-22B shows that an increase in tensile modulus from 363 kpsi to 696 kpsi for virgin PEEK and 20% talc-filled PEEK leads to ~2 fold increase in performance in the 100 kHz to 150 kHz excitation frequency range. This increase in spray performance tracks with the corresponding increase in tensile modulus.

Although the foregoing describes various embodiments by way of illustration and example, the skilled artisan will appreciate that various changes and modifications may be practiced within the spirit and scope of the present application.

What is claimed is:

1. A device for delivering a fluid to a target, the device comprising:

a housing;

a reservoir disposed within the housing for receiving a volume of fluid; and an ejector mechanism in fluid communication with the reservoir and configured to eject a stream of droplets, the ejector mechanism comprising an ejector plate having a first surface in fluid communication with a fluid delivery area of the reservoir, and a second surface coupled to a polymeric generator plate and a piezoelectric actuator;

the polymeric generator plate having a first fluid intake surface coupled to the ejector plate and in fluid communication with a fluid delivery area of the reservoir, a second fluid exit surface, and a plurality of openings formed through its thickness, the plurality of openings having an average opening diameter at the second fluid exit surface of from about 20 μm to about 100 μm, which average opening diameter at the second fluid exit surface is smaller than the average opening diameter at the first fluid intake surface; and the piezoelectric actuator being operable to oscillate the ejector plate, and thereby the polymeric generator plate, at a frequency and generate a directed stream of droplets;

wherein one or more of said plurality of openings are shaped so as to comprise a fluid entrance orifice, an entrance cavity, a capillary channel, and a fluid exit orifice, the capillary channel having a length in the range of from about 70 μm to about 120 μm.

2. The device of claim 1, wherein the plurality of openings are configured to provide desired three-dimensional geometry and shape and are formed via laser micromachining.

3. The device of claim 1, wherein the polymer generator plate is formed from a material selected from the group consisting of: ultrahigh molecular weight polyethylene (UHMWPE), polyimide, polyether ether ketone (PEEK), talc-filled PEEK, polyvinylidine fluoride (PVDF), and polyetherimide.

4. The device of claim 1, wherein the ejector plate has a central open region aligned with the polymeric generator plate, and the piezoelectric actuator is coupled to a peripheral region of the ejector plate so as to not obstruct the plurality of openings of the polymeric generator plate.

5. The device of claim 4, wherein the plurality of openings of the polymeric generator plate are disposed in a center region of the polymeric generator plate that is uncovered by the piezoelectric actuator and aligned with the central open region of the ejector plate.

6. The device of claim 5, wherein the polymeric generator plate has a reduced size relative to the ejector plate, and the size of the polymeric generator plate is determined, at least in part, by the area occupied by the center region and the arrangement of the plurality of openings.

7. The device of claim 1, having an average ejected droplet diameter greater than 15 microns, the stream of droplets having low entrained airflow such that the stream of droplets deposit on a target during use.

8. An ejector mechanism configured to eject a stream of droplets, the ejector mechanism comprising:

an ejector plate having a first surface in fluid communication with a fluid delivery area of a reservoir, and a second surface coupled to a polymeric generator plate and a piezoelectric actuator;

the polymeric generator plate having a first fluid intake surface coupled to the ejector plate, a second fluid exit surface, and a plurality of openings formed through its thickness, the plurality of openings having an average opening diameter at the second fluid exit surface of from about 20 μm to about 100 μm, which average opening diameter at the second fluid exit surface is smaller than the average opening diameter at the first fluid intake surface; and the piezoelectric actuator being operable to oscillate the ejector plate, and thereby the polymeric generator plate, at a frequency and generate a directed stream of droplets wherein one or more of said plurality of openings are shaped so as to comprise a fluid entrance orifice, an entrance cavity, a capillary channel, and a fluid exit orifice, the capillary channel having a length in the range of from about 70 μm to about 120 μm.

9. The ejector mechanism of claim 8, wherein the polymer generator plate is formed from a material selected from the group consisting of: ultrahigh molecular weight polyethylene (UHMWPE), polyimide, polyether ether ketone (PEEK), talc-filled PEEK, polyvinylidine fluoride (PVDF), and polyetherimide.

10. The ejector mechanism of claim 8, wherein the ejector plate has a central open region aligned with the polymeric generator plate, and the piezoelectric actuator is coupled to a peripheral region of the ejector plate so as to not obstruct the plurality of openings of the polymeric generator plate.

11. The ejector mechanism of claim 10, wherein the plurality of openings of the polymeric generator plate are disposed in a center region of the polymeric generator plate that is uncovered by the piezoelectric actuator and aligned with the central open region of the ejector plate.

12. The ejector mechanism of claim 11, wherein the polymeric generator plate has a reduced size relative to the ejector plate, and the size of the polymeric generator plate is determined, at least in part, by the area occupied by the center region and the arrangement of the plurality of openings.

* * * * *